(12) United States Patent
Gifford, III et al.

(10) Patent No.: US 10,350,004 B2
(45) Date of Patent: Jul. 16, 2019

(54) INTRAVASCULAR TREATMENT CATHETERS

(71) Applicant: Twelve, Inc., Menlo Park, CA (US)

(72) Inventors: Hanson Gifford, III, Woodside, CA (US); Mark Deem, Mountain View, CA (US); Stephen Boyd, Murrieta, CA (US)

(73) Assignee: Twelve, Inc., Menlo Park, CA (US)

( * ) Notice: Subject to any disclaimer, the term of this patent is extended or adjusted under 35 U.S.C. 154(b) by 235 days.

(21) Appl. No.: 15/212,797

(22) Filed: Jul. 18, 2016

(65) Prior Publication Data

US 2017/0014183 A1 Jan. 19, 2017

Related U.S. Application Data

(60) Continuation of application No. 13/692,613, filed on Dec. 3, 2012, now Pat. No. 9,414,852, which is a
(Continued)

(51) Int. Cl.
*A61B 8/12* (2006.01)
*A61F 2/24* (2006.01)
(Continued)

(52) U.S. Cl.
CPC ........ *A61B 18/1492* (2013.01); *A61B 17/221* (2013.01); *A61B 17/2202* (2013.01);
(Continued)

(58) Field of Classification Search
CPC ............ A61N 2007/0039; A61N 7/022; A61N 25/04; A61M 2025/105; A61M 25/04;
A61F 2/2445; A61B 2018/0262; A61B 2018/0022; A61B 2017/2215; A61B 2017/22098; A61B 2017/22079; A61B 2017/22069; A61B 2017/22061; A61B 2017/22038; A61B 18/18; A61B 18/1492; A61B 18/02; A61B 17/320758; A61B 17/221; A61B 17/2202; A61B 17/22012; A61B 8/12
See application file for complete search history.

(56) References Cited

U.S. PATENT DOCUMENTS 931,795 A  8/1909  James
3,526,219 A  9/1970  Lewis
(Continued)

FOREIGN PATENT DOCUMENTS

CA  2384866  4/2001
CA  2575458  3/2006
(Continued)

OTHER PUBLICATIONS

US 8,398,630 B2, 03/2013, Demarais et al. (withdrawn)
(Continued)

*Primary Examiner* — Jocelin C Tanner

(57) ABSTRACT

The present invention provides devices and methods for decalcifying an aortic valve. The methods and devices of the present invention break up or obliterate calcific deposits in and around the aortic valve through application or removal of heat energy from the calcific deposits.

11 Claims, 46 Drawing Sheets

Related U.S. Application Data continuation of application No. 12/870,270, filed on Aug. 27, 2010, now abandoned, which is a division of application No. 11/299,246, filed on Dec. 9, 2005, now Pat. No. 7,803,168.

(60) Provisional application No. 60/698,297, filed on Jul. 11, 2005, provisional application No. 60/662,764, filed on Mar. 16, 2005, provisional application No. 60/635,275, filed on Dec. 9, 2004.

(51) Int. Cl.

| | |
|---|---|
| *A61N 7/00* | (2006.01) |
| *A61N 7/02* | (2006.01) |
| *A61B 17/22* | (2006.01) |
| *A61B 18/00* | (2006.01) |
| *A61B 18/02* | (2006.01) |
| *A61B 18/14* | (2006.01) |
| *A61B 18/18* | (2006.01) |
| *A61M 25/04* | (2006.01) |
| *A61M 25/10* | (2013.01) |
| *A61B 17/221* | (2006.01) |
| *A61B 17/3207* | (2006.01) |

(52) U.S. Cl.
CPC ............... *A61B 17/22012* (2013.01); *A61B 17/320758* (2013.01); *A61B 18/02* (2013.01); *A61F 2/2445* (2013.01); *A61M 25/04* (2013.01); *A61N 7/022* (2013.01); *A61B 8/12* (2013.01); *A61B 18/18* (2013.01); *A61B 2017/2215* (2013.01); *A61B 2017/22038* (2013.01); *A61B 2017/22061* (2013.01); *A61B 2017/22069* (2013.01); *A61B 2017/22079* (2013.01); *A61B 2017/22098* (2013.01); *A61B 2018/00011* (2013.01); *A61B 2018/0022* (2013.01); *A61B 2018/0262* (2013.01); *A61M 2025/105* (2013.01); *A61N 2007/0039* (2013.01)

(56) References Cited

U.S. PATENT DOCUMENTS

| | | | |
|---|---|---|---|
| 3,565,062 A | 2/1971 | Kuris | |
| 3,589,363 A | 6/1971 | Banko et al. | |
| 3,667,474 A | 6/1972 | Lapkin et al. | |
| 3,752,162 A | 8/1973 | Newash | |
| 3,823,717 A | 7/1974 | Pohlman et al. | |
| 3,861,391 A | 1/1975 | Antonevich et al. | |
| 3,896,811 A | 7/1975 | Storz | |
| 4,042,979 A | 8/1977 | Angell | |
| 4,046,150 A | 9/1977 | Schwartz et al. | |
| 4,188,952 A | 2/1980 | Loschilov et al. | |
| 4,431,006 A | 2/1984 | Trimmer et al. | |
| 4,445,509 A | 5/1984 | Auth | |
| 4,484,579 A | 11/1984 | Meno et al. | |
| 4,587,958 A | 5/1986 | Noguchi et al. | |
| 4,589,419 A | 5/1986 | Laughlin et al. | |
| 4,646,736 A | 3/1987 | Auth | |
| 4,692,139 A | 9/1987 | Stiles | |
| 4,709,698 A | 12/1987 | Johnston et al. | |
| 4,747,821 A | 5/1988 | Kensey et al. | |
| 4,750,902 A | 6/1988 | Wuchinich et al. | |
| 4,777,951 A | 10/1988 | Cribier et al. | |
| 4,787,388 A | 11/1988 | Hofmann | |
| 4,790,812 A | 12/1988 | Hawkins, Jr. et al. | |
| 4,796,629 A | 1/1989 | Grayzel | |
| 4,808,153 A | 2/1989 | Parisi | |
| 4,819,751 A | 4/1989 | Shimada et al. | |
| 4,824,436 A | 4/1989 | Wolinsky | |
| 4,841,977 A | 6/1989 | Griffith et al. | |
| 4,870,953 A | 10/1989 | DonMicheal et al. | |
| 4,878,495 A | 11/1989 | Grayzel | |
| 4,898,575 A | 2/1990 | Fischell et al. | |
| 4,909,252 A | 3/1990 | Goldberger | |
| 4,919,133 A | 4/1990 | Chiang | |
| 4,920,954 A | 5/1990 | Alliger et al. | |
| 4,936,281 A | 6/1990 | Stasz | |
| 4,960,411 A | 10/1990 | Buchbinder | |
| 4,986,830 A | 1/1991 | Owens et al. | |
| 4,990,134 A | 2/1991 | Auth | |
| 5,058,570 A | 10/1991 | Idemoto et al. | |
| 5,069,664 A | 12/1991 | Guess et al. | |
| 5,071,424 A | 12/1991 | Reger | |
| 5,076,276 A | 12/1991 | Sakurai et al. | |
| 5,078,717 A | 1/1992 | Parins et al. | |
| 5,087,244 A | 2/1992 | Wolinsky et al. | |
| 5,102,402 A | 4/1992 | Dror et al. | |
| 5,106,302 A | 4/1992 | Farzin-Nia et al. | |
| 5,156,610 A | 10/1992 | Reger | |
| 5,158,564 A | 10/1992 | Schnepp-Pesch et al. | |
| 5,190,540 A | 3/1993 | Lee | |
| 5,211,651 A | 5/1993 | Reger et al. | |
| 5,248,296 A | 9/1993 | Alliger | |
| 5,255,679 A | 10/1993 | Imran | |
| 5,267,954 A | 12/1993 | Nita | |
| 5,269,291 A | 12/1993 | Carter | |
| 5,282,484 A | 2/1994 | Reger | |
| 5,295,958 A | 3/1994 | Shturman | |
| 5,304,115 A | 4/1994 | Pflueger et al. | |
| 5,304,120 A | 4/1994 | Crandell et al. | |
| 5,306,250 A | 4/1994 | March et al. | |
| 5,314,407 A | 5/1994 | Auth et al. | |
| 5,318,014 A | 6/1994 | Carter | |
| 5,326,341 A | 7/1994 | Lew et al. | |
| 5,344,395 A | 9/1994 | Whalen et al. | |
| 5,345,936 A | 9/1994 | Pomeranz et al. | |
| 5,356,418 A | 10/1994 | Shturman | |
| 5,397,293 A | 3/1995 | Alliger et al. | |
| 5,411,025 A * | 5/1995 | Webster, Jr. | 128/642 |
| 5,419,767 A | 5/1995 | Eggers et al. | |
| 5,419,777 A | 5/1995 | Hofling | |
| 5,443,446 A | 8/1995 | Shturman | |
| 5,464,395 A | 11/1995 | Faxon et al. | |
| 5,465,717 A | 11/1995 | Imran et al. | |
| 5,471,982 A | 12/1995 | Edwards et al. | |
| 5,476,495 A | 12/1995 | Kordis et al. | |
| 5,489,297 A | 2/1996 | Duran | |
| 5,496,311 A | 3/1996 | Abele et al. | |
| 5,538,504 A | 7/1996 | Linden et al. | |
| 5,540,679 A | 7/1996 | Fram et al. | |
| 5,571,122 A | 11/1996 | Kelly et al. | |
| 5,584,879 A | 12/1996 | Reimold et al. | |
| 5,588,960 A | 12/1996 | Edwards et al. | |
| 5,588,962 A | 12/1996 | Nicholas et al. | |
| 5,590,654 A | 1/1997 | Prince | |
| 5,609,151 A | 3/1997 | Mulier et al. | |
| 5,636,634 A | 6/1997 | Kordis et al. | |
| 5,662,671 A | 9/1997 | Barbut et al. | |
| 5,665,098 A | 9/1997 | Kelly et al. | |
| 5,667,490 A | 9/1997 | Keith et al. | |
| 5,681,336 A | 10/1997 | Clement et al. | |
| 5,695,507 A | 12/1997 | Auth et al. | |
| 5,704,908 A | 1/1998 | Hofmann et al. | |
| 5,709,874 A | 1/1998 | Hanson et al. | |
| 5,722,401 A | 3/1998 | Pietroski et al. | |
| 5,725,494 A | 3/1998 | Brisken | |
| 5,772,590 A | 6/1998 | Webster, Jr. | |
| 5,782,931 A | 7/1998 | Yang et al. | |
| 5,807,306 A | 9/1998 | Shapland et al. | |
| 5,817,144 A | 10/1998 | Gregory | |
| 5,823,956 A | 10/1998 | Roth et al. | |
| 5,827,229 A | 10/1998 | Auth et al. | |
| 5,829,447 A | 11/1998 | Stevens et al. | |
| 5,840,081 A | 11/1998 | Andersen et al. | |
| 5,843,016 A | 12/1998 | Lugnani et al. | |
| 5,848,969 A | 12/1998 | Panescu et al. | |
| 5,860,974 A | 1/1999 | Abele | |
| 5,865,801 A | 2/1999 | Houser | |
| 5,873,811 A | 2/1999 | Wang et al. | |
| 5,876,374 A | 3/1999 | Alba et al. | |

(56) References Cited

U.S. PATENT DOCUMENTS

| | | |
|---|---|---|
| 5,904,679 A | 5/1999 | Clayman |
| 5,910,129 A * | 6/1999 | Koblish et al. .... A61M 25/0043 604/95 |
| 5,916,227 A | 6/1999 | Keith et al. |
| 5,924,424 A | 7/1999 | Stevens et al. |
| 5,938,670 A | 8/1999 | Keith et al. |
| 5,954,742 A | 9/1999 | Osypka |
| 5,957,882 A | 9/1999 | Nita et al. |
| 5,989,208 A | 11/1999 | Nita |
| 5,997,497 A | 12/1999 | Nita et al. |
| 6,004,269 A | 12/1999 | Crowley et al. |
| 6,010,522 A | 1/2000 | Barbut et al. |
| 6,014,590 A | 1/2000 | Whayne et al. |
| 6,024,740 A | 2/2000 | Lesh et al. |
| 6,036,689 A | 3/2000 | Tu et al. |
| 6,047,700 A | 4/2000 | Eggers et al. |
| 6,056,744 A | 5/2000 | Edwards |
| 6,079,414 A | 6/2000 | Roth |
| 6,117,101 A | 9/2000 | Diederich et al. |
| 6,117,128 A | 9/2000 | Gregory |
| RE36,939 E | 10/2000 | Tachibana et al. |
| 6,129,725 A | 10/2000 | Tu et al. |
| 6,132,444 A | 10/2000 | Shturman et al. |
| 6,149,647 A | 11/2000 | Tu et al. |
| 6,152,899 A | 11/2000 | Farley et al. |
| 6,165,187 A | 12/2000 | Reger |
| 6,168,579 B1 | 1/2001 | Tsugita |
| 6,211,247 B1 | 4/2001 | Goodman |
| 6,216,044 B1 | 4/2001 | Kordis |
| 6,217,595 B1 | 4/2001 | Shturman et al. |
| 6,219,577 B1 | 4/2001 | Brown, III et al. |
| 6,231,513 B1 | 5/2001 | Daum et al. |
| 6,231,516 B1 | 5/2001 | Keilman et al. |
| 6,235,044 B1 | 5/2001 | Root et al. |
| 6,236,883 B1 | 5/2001 | Ciaccio et al. |
| 6,238,389 B1 | 5/2001 | Paddock et al. |
| 6,245,045 B1 | 6/2001 | Stratienko |
| 6,254,635 B1 | 7/2001 | Schroeder et al. |
| 6,283,947 B1 | 9/2001 | Mirzaee |
| 6,283,951 B1 | 9/2001 | Flaherty et al. |
| 6,292,695 B1 | 9/2001 | Webster, Jr. et al. |
| 6,295,712 B1 | 10/2001 | Shturman et al. |
| 6,296,619 B1 | 10/2001 | Brisken et al. |
| 6,302,870 B1 | 10/2001 | Jacobsen et al. |
| 6,309,379 B1 | 10/2001 | Willard et al. |
| 6,309,399 B1 | 10/2001 | Barbut et al. |
| 6,319,251 B1 | 11/2001 | Tu et al. |
| 6,321,109 B2 | 11/2001 | Ben-Haim et al. |
| 6,322,559 B1 | 11/2001 | Daulton et al. |
| 6,346,074 B1 | 2/2002 | Roth |
| 6,353,751 B1 | 3/2002 | Swanson et al. |
| 6,357,447 B1 | 3/2002 | Swanson et al. |
| 6,379,373 B1 | 4/2002 | Sawhney et al. |
| 6,389,311 B1 | 5/2002 | Whayne et al. |
| 6,389,314 B2 | 5/2002 | Feiring |
| 6,401,720 B1 | 6/2002 | Stevens et al. |
| 6,405,732 B1 | 6/2002 | Edwards et al. |
| 6,409,723 B1 | 6/2002 | Edwards |
| 6,423,032 B2 | 7/2002 | Parodi |
| 6,454,737 B1 | 9/2002 | Nita et al. |
| 6,454,757 B1 | 9/2002 | Nita et al. |
| 6,454,775 B1 | 9/2002 | Demarais et al. |
| 6,484,052 B1 | 11/2002 | Visuri et al. |
| 6,494,890 B1 | 12/2002 | Shturman et al. |
| 6,494,891 B1 | 12/2002 | Cornish et al. |
| 6,497,711 B1 | 12/2002 | Plaia et al. |
| 6,500,174 B1 | 12/2002 | Maguire et al. |
| 6,505,080 B1 | 1/2003 | Sutton |
| 6,511,496 B1 | 1/2003 | Huter et al. |
| 6,514,236 B1 | 2/2003 | Stratienko |
| 6,524,274 B1 | 2/2003 | Rosenthal et al. |
| 6,558,382 B2 | 5/2003 | Jahns et al. |
| 6,562,034 B2 | 5/2003 | Edwards et al. |
| 6,565,588 B1 | 5/2003 | Clement et al. |
| 6,572,612 B2 | 6/2003 | Stewart et al. |
| 6,575,933 B1 | 6/2003 | Wittenberger et al. |
| 6,579,308 B1 | 6/2003 | Jansen et al. |
| 6,582,462 B1 | 6/2003 | Andersen et al. |
| 6,595,959 B1 | 7/2003 | Stratienko |
| 6,616,624 B1 | 9/2003 | Kieval |
| 6,623,452 B2 | 9/2003 | Chien et al. |
| 6,623,453 B1 | 9/2003 | Guibert et al. |
| 6,638,288 B1 | 10/2003 | Shturman et al. |
| 6,640,120 B1 | 10/2003 | Swanson et al. |
| 6,645,223 B2 | 11/2003 | Boyle et al. |
| 6,648,854 B1 | 11/2003 | Patterson et al. |
| 6,651,672 B2 | 11/2003 | Roth |
| 6,658,279 B2 | 12/2003 | Swanson et al. |
| 6,673,090 B2 | 1/2004 | Root et al. |
| 6,679,268 B2 | 1/2004 | Stevens et al. |
| 6,689,086 B1 | 2/2004 | Nita et al. |
| 6,689,148 B2 | 2/2004 | Sawhney et al. |
| 6,692,490 B1 | 2/2004 | Edwards |
| 6,692,738 B2 | 2/2004 | MacLaughlin et al. |
| 6,695,830 B2 | 2/2004 | Vigil et al. |
| 6,702,748 B2 | 3/2004 | Nita et al. |
| 6,706,011 B1 | 3/2004 | Murphy-Chutorian et al. |
| 6,714,822 B2 | 3/2004 | King et al. |
| 6,723,064 B2 | 4/2004 | Babaev |
| 6,746,463 B1 | 6/2004 | Schwartz |
| 6,748,255 B2 | 6/2004 | Fuimaono et al. |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,763,261 B2 | 7/2004 | Casscells, III et al. |
| 6,767,544 B2 | 7/2004 | Brooks et al. |
| 6,780,183 B2 | 8/2004 | Jimenez, Jr. et al. |
| 6,788,977 B2 | 9/2004 | Fenn et al. |
| 6,811,801 B2 | 11/2004 | Nguyen et al. |
| 6,818,001 B2 | 11/2004 | Wulfman et al. |
| 6,829,497 B2 | 12/2004 | Mogul |
| 6,830,568 B1 | 12/2004 | Kesten et al. |
| 6,837,886 B2 | 1/2005 | Collins et al. |
| 6,843,797 B2 | 1/2005 | Nash et al. |
| 6,845,267 B2 | 1/2005 | Harrison et al. |
| 6,849,075 B2 | 2/2005 | Bertolero et al. |
| 6,852,118 B2 | 2/2005 | Shturman et al. |
| 6,855,123 B2 | 2/2005 | Nita |
| 6,869,431 B2 | 3/2005 | Maguire et al. |
| 6,869,439 B2 | 3/2005 | White et al. |
| 6,893,414 B2 | 5/2005 | Goble et al. |
| 6,974,456 B2 | 12/2005 | Edwards et al. |
| 6,978,174 B2 | 12/2005 | Gelfand et al. |
| 6,991,617 B2 | 1/2006 | Hektner et al. |
| 7,022,105 B1 | 4/2006 | Edwards |
| 7,066,904 B2 | 6/2006 | Rosenthal et al. |
| 7,100,614 B2 | 9/2006 | Stevens et al. |
| 7,104,987 B2 | 9/2006 | Biggs et al. |
| 7,122,033 B2 | 10/2006 | Wood |
| 7,127,284 B2 | 10/2006 | Seward |
| 7,141,041 B2 | 11/2006 | Seward |
| 7,162,303 B2 | 1/2007 | Levin et al. |
| 7,165,551 B2 | 1/2007 | Edwards et al. |
| 7,184,811 B2 | 2/2007 | Phan et al. |
| 7,197,354 B2 | 3/2007 | Sobe |
| 7,200,445 B1 | 4/2007 | Dalbec et al. |
| 7,241,273 B2 | 7/2007 | Maguire et al. |
| 7,241,736 B2 | 7/2007 | Hunter et al. |
| 7,273,469 B1 | 9/2007 | Chan et al. |
| 7,291,146 B2 | 11/2007 | Steinke et al. |
| 7,297,475 B2 | 11/2007 | Koiwai et al. |
| 7,326,226 B2 | 2/2008 | Root et al. |
| 7,326,235 B2 | 2/2008 | Edwards |
| 7,329,236 B2 | 2/2008 | Kesten et al. |
| 7,335,192 B2 | 2/2008 | Keren et al. |
| 7,364,566 B2 | 4/2008 | Elkins et al. |
| 7,396,355 B2 | 7/2008 | Goldman et al. |
| 7,407,502 B2 | 8/2008 | Strul et al. |
| 7,407,671 B2 | 8/2008 | McBride et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,465,298 B2 | 12/2008 | Seward et al. |
| 7,481,803 B2 | 1/2009 | Kesten et al. |

(56) References Cited

U.S. PATENT DOCUMENTS

| | | |
|---|---|---|
| 7,485,104 B2 | 2/2009 | Kieval |
| 7,507,235 B2 | 3/2009 | Keogh et al. |
| 7,529,589 B2 | 5/2009 | Williams et al. |
| 7,532,938 B2 | 5/2009 | Machado et al. |
| 7,540,870 B2 | 6/2009 | Babaev |
| 7,556,624 B2 | 7/2009 | Laufer et al. |
| 7,558,625 B2 | 7/2009 | Levin et al. |
| 7,563,247 B2 | 7/2009 | Maguire et al. |
| 7,599,730 B2 | 10/2009 | Hunter et al. |
| 7,632,268 B2 | 12/2009 | Edwards et al. |
| 7,640,046 B2 | 12/2009 | Pastore et al. |
| 7,653,438 B2 | 1/2010 | Deem et al. |
| 7,666,163 B2 | 2/2010 | Seward et al. |
| 7,670,335 B2 | 3/2010 | Keidar |
| 7,678,123 B2 | 3/2010 | Chanduszko |
| 7,691,080 B2 | 4/2010 | Seward et al. |
| 7,706,882 B2 | 4/2010 | Francischelli et al. |
| 7,744,584 B2 | 6/2010 | Seward et al. |
| 7,766,892 B2 | 8/2010 | Keren et al. |
| 7,803,168 B2 | 9/2010 | Gifford et al. |
| 7,837,720 B2 | 11/2010 | Mon |
| 7,850,685 B2 | 12/2010 | Kunis et al. |
| 7,854,734 B2 | 12/2010 | Biggs et al. |
| 7,905,862 B2 | 3/2011 | Sampson |
| 7,917,208 B2 | 3/2011 | Yomtov et al. |
| 7,972,330 B2 | 7/2011 | Alejandro et al. |
| 8,007,495 B2 | 8/2011 | McDaniel et al. |
| 8,016,786 B2 | 9/2011 | Seward et al. |
| 8,019,435 B2 | 9/2011 | Hastings et al. |
| 8,021,362 B2 | 9/2011 | Deem et al. |
| 8,027,740 B2 | 9/2011 | Altman et al. |
| 8,119,183 B2 | 2/2012 | O'Donoghue et al. |
| 8,131,371 B2 | 3/2012 | Demarais et al. |
| 8,162,933 B2 | 4/2012 | Francischelli et al. |
| 8,257,724 B2 | 9/2012 | Cromack et al. |
| 8,257,725 B2 | 9/2012 | Cromack et al. |
| 8,263,104 B2 | 9/2012 | Ho et al. |
| 8,295,902 B2 | 10/2012 | Salahieh et al. |
| 8,317,776 B2 | 11/2012 | Ferren et al. |
| 8,317,810 B2 | 11/2012 | Stangenes et al. |
| 8,337,492 B2 | 12/2012 | Kunis et al. |
| 8,364,237 B2 | 1/2013 | Stone et al. |
| 8,388,680 B2 | 3/2013 | Starksen et al. |
| 8,396,548 B2 | 3/2013 | Perry et al. |
| 8,399,443 B2 | 3/2013 | Seward |
| 8,403,881 B2 | 3/2013 | Ferren et al. |
| 8,403,983 B2 | 3/2013 | Quadri et al. |
| 8,409,172 B2 | 4/2013 | Moll et al. |
| 8,465,752 B2 | 6/2013 | Seward |
| 8,562,573 B1 | 10/2013 | Fischell |
| 8,584,681 B2 | 11/2013 | Danek et al. |
| 8,663,190 B2 | 3/2014 | Fischell et al. |
| 8,708,995 B2 | 4/2014 | Seward et al. |
| 8,721,590 B2 | 5/2014 | Seward et al. |
| 8,740,849 B1 | 6/2014 | Fischell et al. |
| 8,740,895 B2 | 6/2014 | Mayse et al. |
| 8,758,334 B2 | 6/2014 | Coe et al. |
| 8,777,943 B2 | 7/2014 | Mayse et al. |
| 8,909,316 B2 | 12/2014 | Ng |
| 8,951,251 B2 | 2/2015 | Willard |
| 8,975,233 B2 | 3/2015 | Stein et al. |
| 8,979,839 B2 | 3/2015 | De La Rama et al. |
| 9,011,879 B2 | 4/2015 | Seward |
| 9,033,917 B2 | 5/2015 | Magana et al. |
| 9,055,956 B2 | 6/2015 | McRae et al. |
| 9,056,184 B2 | 6/2015 | Stein et al. |
| 9,056,185 B2 | 6/2015 | Fischell et al. |
| 9,108,030 B2 | 8/2015 | Braga |
| 9,114,123 B2 | 8/2015 | Azamian et al. |
| 9,131,983 B2 | 9/2015 | Fischell et al. |
| 9,173,696 B2 | 11/2015 | Schauer et al. |
| 9,179,962 B2 | 11/2015 | Fischell et al. |
| 9,199,065 B2 | 12/2015 | Seward |
| 9,237,925 B2 | 1/2016 | Fischell et al. |
| 9,254,360 B2 | 2/2016 | Fischell et al. |
| 9,278,196 B2 | 3/2016 | Fischell et al. |
| 9,301,795 B2 | 4/2016 | Fischell et al. |
| 9,320,850 B2 | 4/2016 | Fischell et al. |
| 9,414,852 B2 | 8/2016 | Gifford, III et al. |
| 9,414,885 B2 | 8/2016 | Willard |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,629,719 B2 | 4/2017 | Rothstein et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 2001/0000041 A1 | 3/2001 | Selmon et al. |
| 2001/0007070 A1 | 7/2001 | Stewart et al. |
| 2001/0031981 A1 | 10/2001 | Evans et al. |
| 2001/0039419 A1 | 11/2001 | Francischelli et al. |
| 2001/0044591 A1 | 11/2001 | Stevens et al. |
| 2001/0044596 A1 | 11/2001 | Jaafar |
| 2002/0007192 A1 | 1/2002 | Pederson et al. |
| 2002/0077592 A1 | 6/2002 | Barry |
| 2002/0077627 A1* | 6/2002 | Johnson et al. ........ A61B 18/18 606/41 |
| 2002/0082552 A1 | 6/2002 | Ding et al. |
| 2002/0082637 A1 | 6/2002 | Lumauig |
| 2002/0099439 A1 | 7/2002 | Schwartz et al. |
| 2002/0103445 A1 | 8/2002 | Randert et al. |
| 2002/0139379 A1 | 10/2002 | Edwards et al. |
| 2002/0143324 A1 | 10/2002 | Edwards |
| 2002/0151918 A1 | 10/2002 | Lafontaine et al. |
| 2002/0165532 A1 | 11/2002 | Hill et al. |
| 2002/0183682 A1 | 12/2002 | Darvish et al. |
| 2003/0028114 A1 | 2/2003 | Casscells et al. |
| 2003/0050637 A1 | 3/2003 | Maguire et al. |
| 2003/0069619 A1 | 4/2003 | Fenn et al. |
| 2003/0074039 A1 | 4/2003 | Puskas |
| 2003/0082225 A1 | 5/2003 | Mason |
| 2003/0114791 A1 | 6/2003 | Rosenthal et al. |
| 2003/0139689 A1 | 7/2003 | Shturman et al. |
| 2003/0144658 A1 | 7/2003 | Schwartz et al. |
| 2003/0158584 A1 | 8/2003 | Cates et al. |
| 2003/0176816 A1 | 9/2003 | Maguire et al. |
| 2003/0216792 A1 | 11/2003 | Levin et al. |
| 2003/0233099 A1 | 12/2003 | Danaek et al. |
| 2003/0236455 A1 | 12/2003 | Swanson et al. |
| 2004/0006358 A1 | 1/2004 | Wulfman et al. |
| 2004/0019348 A1 | 1/2004 | Stevens et al. |
| 2004/0039412 A1 | 2/2004 | Isshiki et al. |
| 2004/0043030 A1 | 3/2004 | Griffiths et al. |
| 2004/0044286 A1 | 3/2004 | Hossack et al. |
| 2004/0044350 A1 | 3/2004 | Martin et al. |
| 2004/0057955 A1 | 3/2004 | O'Brien et al. |
| 2004/0062852 A1 | 4/2004 | Schroeder et al. |
| 2004/0064090 A1 | 4/2004 | Keren et al. |
| 2004/0064093 A1 | 4/2004 | Hektner et al. |
| 2004/0073243 A1 | 4/2004 | Sepetka et al. |

(56) References Cited

U.S. PATENT DOCUMENTS

| | | |
|---|---|---|
| 2004/0082910 A1 | 4/2004 | Constantz et al. |
| 2004/0082978 A1 | 4/2004 | Harrison et al. |
| 2004/0088002 A1 | 5/2004 | Boyle et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0103516 A1 | 6/2004 | Bolduc et al. |
| 2004/0117032 A1 | 6/2004 | Roth |
| 2004/0122421 A1 | 6/2004 | Wood |
| 2004/0127979 A1 | 7/2004 | Wilson et al. |
| 2004/0186468 A1 | 9/2004 | Edwards |
| 2004/0199191 A1 | 10/2004 | Schwartz |
| 2004/0220556 A1 | 11/2004 | Cooper et al. |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243097 A1 | 12/2004 | Falotico et al. |
| 2004/0243162 A1 | 12/2004 | Wulfman et al. |
| 2004/0253304 A1 | 12/2004 | Gross et al. |
| 2005/0007219 A1 | 1/2005 | Ma et al. |
| 2005/0075662 A1 | 4/2005 | Pedersen et al. |
| 2005/0090820 A1 | 4/2005 | Cornelius et al. |
| 2005/0096647 A1* | 5/2005 | Steinke et al. ...... A61B 18/1492 606/41 |
| 2005/0149173 A1 | 7/2005 | Hunter et al. |
| 2005/0149175 A1 | 7/2005 | Hunter et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165391 A1 | 7/2005 | Maguire et al. |
| 2005/0165467 A1 | 7/2005 | Hunter et al. |
| 2005/0175661 A1 | 8/2005 | Hunter et al. |
| 2005/0175662 A1 | 8/2005 | Hunter et al. |
| 2005/0177103 A1 | 8/2005 | Hunter et al. |
| 2005/0181004 A1 | 8/2005 | Hunter et al. |
| 2005/0182479 A1 | 8/2005 | Bonsignore et al. |
| 2005/0186242 A1 | 8/2005 | Hunter et al. |
| 2005/0186243 A1 | 8/2005 | Hunter et al. |
| 2005/0192638 A1 | 9/2005 | Gelfand et al. |
| 2005/0228286 A1 | 10/2005 | Messerly et al. |
| 2005/0267556 A1 | 12/2005 | Shuros et al. |
| 2005/0283195 A1 | 12/2005 | Pastore et al. |
| 2006/0018949 A1 | 1/2006 | Ammon et al. |
| 2006/0025821 A1 | 2/2006 | Gelfand et al. |
| 2006/0041277 A1 | 2/2006 | Deem et al. |
| 2006/0111672 A1 | 5/2006 | Seward |
| 2006/0189941 A1 | 8/2006 | Seward et al. |
| 2006/0240070 A1 | 10/2006 | Cromack et al. |
| 2006/0247618 A1 | 11/2006 | Kaplan et al. |
| 2006/0247619 A1 | 11/2006 | Kaplan et al. |
| 2006/0263393 A1 | 11/2006 | Demopulos et al. |
| 2006/0280858 A1 | 12/2006 | Kokish |
| 2007/0066959 A1 | 3/2007 | Seward |
| 2007/0078620 A1 | 4/2007 | Seward et al. |
| 2007/0100318 A1 | 5/2007 | Seward et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0106293 A1 | 5/2007 | Oral et al. |
| 2007/0118107 A1 | 5/2007 | Francischelli et al. |
| 2007/0207186 A1 | 9/2007 | Scanlon et al. |
| 2007/0208134 A1 | 9/2007 | Hunter et al. |
| 2007/0219576 A1 | 9/2007 | Cangialosi |
| 2007/0248639 A1 | 10/2007 | Demopulos et al. |
| 2007/0254833 A1 | 11/2007 | Hunter et al. |
| 2007/0269385 A1 | 11/2007 | Yun et al. |
| 2007/0278103 A1 | 12/2007 | Hoerr et al. |
| 2007/0287994 A1 | 12/2007 | Patel |
| 2007/0299043 A1 | 12/2007 | Hunter et al. |
| 2008/0004596 A1 | 1/2008 | Yun et al. |
| 2008/0039746 A1 | 2/2008 | Hissong et al. |
| 2008/0045890 A1 | 2/2008 | Seward et al. |
| 2008/0064957 A1 | 3/2008 | Spence |
| 2008/0082109 A1 | 4/2008 | Moll et al. |
| 2008/0086072 A1 | 4/2008 | Bonutti et al. |
| 2008/0097426 A1 | 4/2008 | Root et al. |
| 2008/0172035 A1 | 7/2008 | Starksen et al. |
| 2008/0208162 A1 | 8/2008 | Joshi |
| 2008/0213331 A1 | 9/2008 | Gelfand et al. |
| 2008/0245371 A1 | 10/2008 | Gruber |
| 2008/0317818 A1 | 12/2008 | Griffith et al. |
| 2009/0024195 A1 | 1/2009 | Rezai et al. |
| 2009/0074828 A1 | 3/2009 | Alexis et al. |
| 2009/0076409 A1 | 3/2009 | Wu et al. |
| 2009/0105631 A1 | 4/2009 | Kieval |
| 2009/0142306 A1 | 6/2009 | Seward et al. |
| 2009/0156988 A1 | 6/2009 | Ferren et al. |
| 2009/0157057 A1 | 6/2009 | Ferren et al. |
| 2009/0203962 A1 | 8/2009 | Miller et al. |
| 2009/0216317 A1 | 8/2009 | Cromack et al. |
| 2009/0221955 A1 | 9/2009 | Babaev |
| 2010/0023088 A1 | 1/2010 | Stack et al. |
| 2010/0049186 A1 | 2/2010 | Ingle et al. |
| 2010/0069837 A1 | 3/2010 | Rassat et al. |
| 2010/0087782 A1 | 4/2010 | Ghaffari et al. |
| 2010/0137860 A1 | 6/2010 | Demarais et al. |
| 2010/0168737 A1 | 7/2010 | Grunewald |
| 2010/0191232 A1 | 7/2010 | Boveda |
| 2010/0204560 A1 | 8/2010 | Salahieh et al. |
| 2010/0217162 A1 | 8/2010 | Hissong et al. |
| 2010/0222851 A1 | 9/2010 | Deem et al. |
| 2010/0228122 A1 | 9/2010 | Keenan et al. |
| 2010/0249702 A1 | 9/2010 | Magana et al. |
| 2010/0256616 A1 | 10/2010 | Katoh et al. |
| 2010/0268217 A1 | 10/2010 | Habib |
| 2010/0286684 A1 | 11/2010 | Hata et al. |
| 2010/0324472 A1 | 12/2010 | Wulfman |
| 2010/0324554 A1 | 12/2010 | Gifford et al. |
| 2011/0104060 A1 | 5/2011 | Seward |
| 2011/0104061 A1 | 5/2011 | Seward |
| 2011/0118726 A1 | 5/2011 | De la rama et al. |
| 2011/0137155 A1 | 6/2011 | Weber et al. |
| 2011/0166499 A1 | 7/2011 | Demarais et al. |
| 2011/0182912 A1 | 7/2011 | Evans et al. |
| 2011/0184337 A1 | 7/2011 | Evans et al. |
| 2011/0202098 A1 | 8/2011 | Demarais et al. |
| 2011/0213231 A1 | 9/2011 | Hall et al. |
| 2011/0257622 A1 | 10/2011 | Salahieh et al. |
| 2011/0301587 A1 | 12/2011 | Deem et al. |
| 2011/0306851 A1 | 12/2011 | Wang |
| 2012/0029500 A1 | 2/2012 | Jenson |
| 2012/0029504 A1 | 2/2012 | Afonso et al. |
| 2012/0029510 A1 | 2/2012 | Haverkost |
| 2012/0071870 A1 | 3/2012 | Salahieh et al. |
| 2012/0116438 A1 | 5/2012 | Salahieh et al. |
| 2012/0157992 A1 | 6/2012 | Smith et al. |
| 2012/0157993 A1 | 6/2012 | Jenson et al. |
| 2012/0172837 A1 | 7/2012 | Demarais et al. |
| 2012/0184952 A1 | 7/2012 | Jenson et al. |
| 2012/0259269 A1 | 10/2012 | Meyer |
| 2012/0265198 A1 | 10/2012 | Crow et al. |
| 2012/0271301 A1 | 10/2012 | Fischell et al. |
| 2012/0296232 A1 | 11/2012 | Ng |
| 2012/0296329 A1 | 11/2012 | Ng |
| 2013/0053732 A1 | 2/2013 | Heuser |
| 2013/0053792 A1 | 2/2013 | Fischell et al. |
| 2013/0066316 A1 | 3/2013 | Steinke et al. |
| 2013/0090651 A1 | 4/2013 | Smith |
| 2013/0090652 A1 | 4/2013 | Jenson |
| 2013/0096550 A1 | 4/2013 | Hill |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0123778 A1 | 5/2013 | Richardson et al. |
| 2013/0158509 A1 | 6/2013 | Consigny et al. |
| 2013/0158536 A1 | 6/2013 | Bloom |
| 2013/0172815 A1 | 7/2013 | Perry et al. |
| 2013/0204131 A1 | 8/2013 | Seward |
| 2013/0226166 A1 | 8/2013 | Chomas et al. |
| 2013/0231658 A1 | 9/2013 | Wang et al. |

(56) References Cited

U.S. PATENT DOCUMENTS

| | | |
|---|---|---|
| 2013/0231659 A1 | 9/2013 | Hill et al. |
| 2013/0245622 A1 | 9/2013 | Wang et al. |
| 2013/0252932 A1 | 9/2013 | Seward |
| 2013/0253623 A1 | 9/2013 | Danek et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0282000 A1 | 10/2013 | Parsonage |
| 2013/0282084 A1 | 10/2013 | Mathur et al. |
| 2013/0289369 A1 | 10/2013 | Margolis |
| 2013/0289555 A1 | 10/2013 | Mayse et al. |
| 2013/0289556 A1 | 10/2013 | Mayse et al. |
| 2013/0289686 A1 | 10/2013 | Masson et al. |
| 2013/0296853 A1 | 11/2013 | Sugimoto et al. |
| 2014/0012231 A1 | 1/2014 | Fischell |
| 2014/0018789 A1 | 1/2014 | Kaplan et al. |
| 2014/0018790 A1 | 1/2014 | Kaplan et al. |
| 2014/0025063 A1 | 1/2014 | Kaplan et al. |
| 2014/0025069 A1 | 1/2014 | Willard et al. |
| 2014/0046319 A1 | 2/2014 | Danek et al. |
| 2014/0058374 A1 | 2/2014 | Edmunds et al. |
| 2014/0074083 A1 | 3/2014 | Horn et al. |
| 2014/0074089 A1 | 3/2014 | Nishii |
| 2014/0107478 A1 | 4/2014 | Seward et al. |
| 2014/0107639 A1 | 4/2014 | Zhang et al. |
| 2014/0135661 A1 | 5/2014 | Garrison et al. |
| 2014/0142408 A1 | 5/2014 | De la rama et al. |
| 2014/0180077 A1 | 6/2014 | Huennekens et al. |
| 2014/0180196 A1 | 6/2014 | Stone et al. |
| 2014/0188103 A1 | 7/2014 | Millett |
| 2014/0200578 A1 | 7/2014 | Groff et al. |
| 2014/0207136 A1 | 7/2014 | De la rama et al. |
| 2014/0228829 A1 | 8/2014 | Schmitt et al. |
| 2014/0243821 A1 | 8/2014 | Salahieh et al. |
| 2014/0246465 A1 | 9/2014 | Peterson et al. |
| 2014/0271717 A1 | 9/2014 | Goshayeshgar et al. |
| 2014/0276124 A1 | 9/2014 | Cholette et al. |
| 2014/0276724 A1 | 9/2014 | Goshayeshgar |
| 2014/0276728 A1 | 9/2014 | Goshayeshgar |
| 2014/0276733 A1 | 9/2014 | Vanscoy et al. |
| 2014/0276742 A1 | 9/2014 | Nabutovsky et al. |
| 2014/0276746 A1 | 9/2014 | Nabutovsky et al. |
| 2014/0276747 A1 | 9/2014 | Abunassar et al. |
| 2014/0276752 A1 | 9/2014 | Wang et al. |
| 2014/0276756 A1 | 9/2014 | Hill |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0296279 A1 | 10/2014 | Seward et al. |
| 2014/0296849 A1 | 10/2014 | Coe et al. |
| 2014/0303569 A1 | 10/2014 | Seward et al. |
| 2014/0303617 A1 | 10/2014 | Shimada |
| 2014/0316400 A1 | 10/2014 | Blix et al. |
| 2014/0316496 A1 | 10/2014 | Masson et al. |
| 2014/0324043 A1 | 10/2014 | Terwey et al. |
| 2014/0330267 A1 | 11/2014 | Harrington |
| 2014/0336494 A1 | 11/2014 | Just et al. |
| 2014/0350533 A1 | 11/2014 | Horvath et al. |
| 2014/0350551 A1 | 11/2014 | Raatikka et al. |
| 2014/0350553 A1 | 11/2014 | Okuyama |
| 2014/0358079 A1 | 12/2014 | Fischell et al. |
| 2014/0364926 A1 | 12/2014 | Nguyen et al. |
| 2014/0378906 A1 | 12/2014 | Fischell et al. |
| 2015/0018656 A1 | 1/2015 | Min et al. |
| 2015/0018818 A1 | 1/2015 | Willard et al. |
| 2015/0105715 A1 | 4/2015 | Pikus et al. |
| 2015/0105772 A1 | 4/2015 | Hill et al. |
| 2015/0112327 A1 | 4/2015 | Willard |
| 2015/0112329 A1 | 4/2015 | Ng |
| 2015/0132409 A1 | 5/2015 | Stein et al. |
| 2015/0148797 A1 | 5/2015 | Willard |
| 2015/0202220 A1 | 7/2015 | Stein et al. |
| 2015/0223866 A1 | 8/2015 | Buelna et al. |
| 2015/0231386 A1 | 8/2015 | Meyer |
| 2015/0289770 A1 | 10/2015 | Wang |
| 2015/0335384 A1 | 11/2015 | Fischell et al. |
| 2015/0343156 A1 | 12/2015 | Fischell et al. |
| 2015/0343175 A1 | 12/2015 | Braga |
| 2015/0351836 A1 | 12/2015 | Prutchi |
| 2015/0374435 A1 | 12/2015 | Cao et al. |
| 2016/0008059 A1 | 1/2016 | Prutchi |
| 2016/0008387 A9 | 1/2016 | Stein et al. |
| 2016/0051465 A1 | 2/2016 | Azamian et al. |
| 2016/0058489 A1 | 3/2016 | Fischell et al. |
| 2016/0157933 A1 | 6/2016 | Hollett et al. |
| 2016/0235464 A1 | 8/2016 | Fischell et al. |
| 2016/0242661 A1 | 8/2016 | Fischell et al. |
| 2016/0310200 A1 | 10/2016 | Wang |
| 2016/0324574 A1 | 11/2016 | Willard |
| 2016/0354137 A1 | 12/2016 | Fischell et al. |
| 2016/0374568 A1 | 12/2016 | Wang |
| 2017/0014183 A1 | 1/2017 | Gifford, III et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0172737 A1 | 6/2017 | Kuetting et al. |
| 2017/0181851 A1 | 6/2017 | Annest |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296339 A1 | 10/2017 | Thambar et al. |
| 2017/0319333 A1 | 11/2017 | Tegels et al. |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |

FOREIGN PATENT DOCUMENTS

| | | |
|---|---|---|
| CN | 2855350 | 1/2007 |
| CN | 101076290 | 11/2007 |
| CN | 102271607 | 12/2011 |
| CN | 102274074 | 12/2011 |
| CN | 202069688 | 12/2011 |
| CN | 202426647 | 9/2012 |
| CN | 102885648 | 1/2013 |
| CN | 102885649 | 1/2013 |
| CN | 102908188 | 2/2013 |
| CN | 102908189 | 2/2013 |
| CN | 202761434 | 3/2013 |
| CN | 202843784 | 4/2013 |
| CN | 202960760 | 6/2013 |
| CN | 103549993 | 2/2014 |
| DE | 29909082 | 7/1999 |
| DE | 10252325 | 5/2004 |
| DE | 10257146 | 6/2004 |
| DE | 202004021941 | 5/2013 |
| DE | 202004021942 | 5/2013 |
| DE | 202004021949 | 5/2013 |
| DE | 202004021951 | 6/2013 |

(56) References Cited

FOREIGN PATENT DOCUMENTS

| | | |
|---|---|---|
| DE | 202004021952 | 6/2013 |
| DE | 202004021953 | 6/2013 |
| DE | 202004021944 | 7/2013 |
| EP | 0233100 | 8/1987 |
| EP | 0497041 | 8/1992 |
| EP | 0774991 | 5/1997 |
| EP | 1180004 | 2/2002 |
| EP | 1512383 | 3/2005 |
| EP | 1634542 | 3/2006 |
| EP | 1782852 | 5/2007 |
| EP | 1802370 | 7/2007 |
| EP | 1874211 | 1/2008 |
| EP | 1009303 | 6/2009 |
| EP | 2329859 | 6/2011 |
| EP | 2352542 | 8/2011 |
| EP | 2400924 | 1/2012 |
| EP | 2429436 | 3/2012 |
| EP | 2429641 | 3/2012 |
| EP | 2457615 A1 | 5/2012 |
| EP | 2498706 | 9/2012 |
| EP | 2519173 | 11/2012 |
| EP | 2528649 | 12/2012 |
| EP | 2558016 | 2/2013 |
| EP | 2598067 | 6/2013 |
| EP | 2598068 | 6/2013 |
| EP | 2598069 | 6/2013 |
| EP | 2640297 | 9/2013 |
| EP | 2656807 | 10/2013 |
| EP | 2675458 | 12/2013 |
| EP | 2694150 | 2/2014 |
| EP | 2694158 | 2/2014 |
| EP | 2709517 | 3/2014 |
| EP | 2717795 | 4/2014 |
| EP | 2731531 | 5/2014 |
| EP | 2747688 | 7/2014 |
| EP | 2457615 B1 | 12/2014 |
| EP | 2819604 | 1/2015 |
| EP | 2844190 | 3/2015 |
| EP | 2870933 | 5/2015 |
| EP | 2874555 | 5/2015 |
| EP | 2885041 | 6/2015 |
| EP | 2895095 | 7/2015 |
| EP | 2911735 | 9/2015 |
| EP | 2914326 | 9/2015 |
| EP | 2950734 | 12/2015 |
| EP | 2954865 | 12/2015 |
| EP | 2967383 | 1/2016 |
| EP | 3011899 | 4/2016 |
| EP | 3019105 | 5/2016 |
| EP | 3060148 | 8/2016 |
| EP | 3229736 | 11/2016 |
| EP | 3102132 | 12/2016 |
| EP | 3132828 | 2/2017 |
| EP | 2470119 | 5/2017 |
| EP | 2999436 | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 2509538 | 9/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256077 | 12/2017 |
| EP | 3258883 | 12/2017 |
| EP | 3273910 | 1/2018 |
| JP | 49009882 | 1/1974 |
| JP | 62181225 | 8/1987 |
| JP | H-06504516 | 5/1994 |
| JP | 3041967 | 10/1997 |
| JP | 2002509756 | 4/2002 |
| JP | 2003510126 | 3/2003 |
| JP | 2004016333 | 1/2004 |
| JP | 2004097807 | 4/2004 |
| JP | 2016083302 | 5/2016 |
| JP | 2016086999 | 5/2016 |
| WO | WO-1990000060 | 1/1990 |
| WO | WO-1992011898 | 7/1992 |
| WO | WO-1992017118 | 10/1992 |
| WO | WO-1992020291 | 11/1992 |
| WO | WO-1994021165 | 9/1994 |
| WO | WO-1994021168 | 9/1994 |
| WO | WO-1995001751 | 1/1995 |
| WO | WO-1995010319 | 4/1995 |
| WO | WO-1996034559 | 11/1996 |
| WO | WO-1997003604 | 2/1997 |
| WO | WO-1997017892 | 5/1997 |
| WO | WO-1997042990 | 11/1997 |
| WO | WO-1999016370 | 4/1999 |
| WO | WO-1999039648 | 8/1999 |
| WO | WO-1999044522 | 9/1999 |
| WO | WO-1999049799 | 10/1999 |
| WO | WO-1999052424 | 10/1999 |
| WO | WO-1999062413 | 12/1999 |
| WO | WO-2000062699 | 10/2000 |
| WO | WO-2001010343 | 2/2001 |
| WO | WO-2001022897 | 4/2001 |
| WO | WO-2001037746 | 5/2001 |
| WO | WO-2001074255 | 10/2001 |
| WO | WO-2002028421 | 4/2002 |
| WO | WO-2002058549 | 8/2002 |
| WO | WO-2003024311 | 3/2003 |
| WO | WO-2003043685 | 5/2003 |
| WO | WO-2003082080 | 10/2003 |
| WO | WO-2004011055 | 2/2004 |
| WO | WO-2004028583 | 4/2004 |
| WO | WO-2004049976 | 6/2004 |
| WO | WO-2004093728 | 11/2004 |
| WO | WO-2004096097 | 11/2004 |
| WO | WO-2004112657 | 12/2004 |
| WO | WO-2005001513 | 1/2005 |
| WO | WO-2005002466 | 1/2005 |
| WO | WO-2005007000 | 1/2005 |
| WO | WO-2005007219 | 1/2005 |
| WO | WO-2005009285 | 2/2005 |
| WO | WO-2005009506 | 2/2005 |
| WO | WO-2005041748 | 5/2005 |
| WO | WO-2006009376 | 1/2006 |
| WO | WO-2006022790 | 3/2006 |
| WO | WO-2006041881 | 4/2006 |
| WO | WO-2006063199 | 6/2006 |
| WO | WO-2006116198 | 11/2006 |
| WO | WO-2009088678 | 7/2009 |
| WO | WO-2010042653 | 4/2010 |
| WO | WO-2010056771 | 5/2010 |
| WO | WO-2011055143 | 5/2011 |
| WO | WO-2011060200 | 5/2011 |
| WO | WO-2011082279 | 7/2011 |
| WO | WO-2011094367 | 8/2011 |
| WO | WO-2011119857 | 9/2011 |
| WO | WO-2011130534 | 10/2011 |
| WO | WO-2011133724 | 10/2011 |
| WO | WO-2012068471 | 5/2012 |
| WO | WO-2012075156 | 6/2012 |
| WO | WO-2012130337 | 10/2012 |
| WO | WO-2012131107 | 10/2012 |
| WO | WO-2012158864 | 11/2012 |
| WO | WO-2012161875 | 11/2012 |
| WO | WO-2012170482 | 12/2012 |
| WO | WO-2013028274 | 2/2013 |
| WO | WO-2013028781 | 2/2013 |
| WO | WO-2013028812 | 2/2013 |
| WO | WO-2013055815 | 4/2013 |
| WO | WO-2013059735 | 4/2013 |
| WO | WO-2013063331 | 5/2013 |
| WO | WO-2013070724 | 5/2013 |
| WO | WO-2013077283 | 5/2013 |
| WO | WO-2013106054 | 7/2013 |
| WO | WO-2013112844 | 8/2013 |

(56) References Cited

FOREIGN PATENT DOCUMENTS

| | | |
|---|---|---|
| WO | WO-2013131046 | 9/2013 |
| WO | WO-2013142217 | 9/2013 |
| WO | WO-2013165920 | 11/2013 |
| WO | WO-2013169741 | 11/2013 |
| WO | WO-2013188689 | 12/2013 |
| WO | WO-2014015065 | 1/2014 |
| WO | WO-2014031167 | 2/2014 |
| WO | WO-2014036160 | 3/2014 |
| WO | WO-2014056460 | 4/2014 |
| WO | WO-2014070820 | 5/2014 |
| WO | WO-2014070999 | 5/2014 |
| WO | WO-2014078301 | 5/2014 |
| WO | WO-2014100226 | 6/2014 |
| WO | WO-2014110579 | 7/2014 |
| WO | WO-2014118733 | 8/2014 |
| WO | WO-2014118734 | 8/2014 |
| WO | WO-2014149550 | 9/2014 |
| WO | WO-2014149552 | 9/2014 |
| WO | WO-2014149553 | 9/2014 |
| WO | WO-2014150204 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014152344 | 9/2014 |
| WO | WO-2014158708 | 10/2014 |
| WO | WO-2014163990 | 10/2014 |
| WO | WO-2014176205 | 10/2014 |
| WO | WO-2014179768 | 11/2014 |
| WO | WO-2014189887 | 11/2014 |
| WO | WO-2014197688 | 12/2014 |
| WO | 2017062640 | 4/2017 |
| WO | 2017096157 | 6/2017 |
| WO | 2017101232 | 6/2017 |
| WO | WO-2017127939 | 8/2017 |
| WO | WO-2017136596 | 8/2017 |
| WO | 2017196511 | 11/2017 |
| WO | 2017196909 | 11/2017 |
| WO | 2017196977 | 11/2017 |
| WO | 2017197064 | 11/2017 |
| WO | 2017218671 | 12/2017 |
| WO | 2018017886 | 1/2018 |

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

ClinicalTrials.gov, Renal Denervation in Patients with uncontrolled Hypertension in Chinese (2011), 6pages. www.clinicaltrials.gov/ct2/show/NCT01390831.

Eick, Olaf, "Temperature Controlled Radiofrequency Ablation." Indian Pacing and Electrophysiology Journal, vol. 2. No. 3, 2002, 8 pages.

European Search Report dated Feb. 22, 2013; Application No. 12180432.2; Applicant: Medtronic Ardian Luxembourg S.a.r.l.; 6 pages.

European Search Report dated Feb. 28, 2013; Application No. 12180427.2; Applicant: Medtronic Ardian Luxembourg S.a.r.l.; 4 pages.

European Search Report dated May 3, 2012; European Patent Application No. 11192511.1; Applicant: Ardian, Inc. (6 pages).

European Search Report dated May 3, 2012; European Patent Application No. 11192514.5; Applicant: Ardian, Inc. (7 pages).

European Search Report dated Jan. 30, 2013; Application No. 12180428.0; Applicant: Medtronic Ardian Luxembourg S.a.r.l.; 6 pages.

European Search Report dated Jan. 30, 2013; Application No. 12180430.6; Applicant: Medtronic Ardian Luxembourg S.a.r.l.; 6 pages.

European Search Report dated Jan. 30, 2013; Application No. 12180431.4; Applicant: Medtronic Ardian Luxembourg S.a.r.l.; 6 pages.

European Search Report dated Jan. 30, 2013; European Application No. 12180426.4; Applicant: Medtronic Ardian Luxembourg S.a.r.l.; 6 pages.

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Prochnau, Dirk et al., Catheter-based renal denervation for drug-resistant hypertension by using a standard electrophysiology catheter; Euro Intervention 2012, vol. 7, pp. 1077-1080.

ThermoCool Irrigated Catheter and Integrated Ablation System, Biosense Webster (2006), 6 pages.

"Optison (Perflutren Protein—Type A Microspheres for Injection, USP)." GE Healthcare. General Electric Company. 1997-2005. Web. May 26, 2005. <http://www.amershamhealth-us.com/optison/.

Bernard et al., "Aortic Valve Area Evolution After Percutaneous Aortic Valvuloplasty," European Heart Journal vol. 11, No. 2, pp. 98-107.

BlueCross BlueShield of Northern Carolina Corporate Medical Policy "Balloon valvuloplasty, Percutaneous", (Jun. 1994).

Bond, et al. "Physics of Ultrasonic Surgery Using Tissue Fragmentation: Part II", Ultrasound Med. & Bio., 1996, vol. 22 (1), pp. 101-117.

Cimino, et al., "Physics of Ultrasonic Surgery Using Tissue Fragmentation: Part I", Ultrasound Med. & Bio., 1996, vol. 22 (1), pp. 89-100.

Cimino, Ultrasonic surgery: power quantification and efficiency optimization. Aesthetic surgery journal, 2001, 233-241.

Cowell et al., "A randomized Trial of Intensive Lipid-Lowering Therapy in Calcific Aortic Stenosis," NEJM vol. 352 No. 23, pp. 2005, 2389-2397.

De Korte et al., "Characterization of plaque components and vulnerability with intravascular ultrasound elastography" Phys. Med. Biol. vol. 45, 2000, pp. 1465-1475.

European Search Report for European App. No. 05853460.3, completed Mar. 13, 2015, 3 pages.

Feldman, "Restenosis Following Successful Balloon Valvuloplasty: Bone Formation in Aortic Valve Leaflets," Cathet Cardiovasc Diagn, vol. 29 No. 1, 1993, pp. 1-7.

Final Office Action for U.S. Appl. No. 12/870,270, dated Jul. 3, 2012, 7 pages.

Final Office Action for U.S. Appl. No. 11/299,246, dated Feb. 17, 2010, 6 pages.

Final Office Action for U.S. Appl. No. 11/299,246, dated Jun. 6, 2008, 5 pages.

Final Office Action for U.S. Appl. No. 13/692,613, dated Nov. 12, 2015, 14 pages.

Fitzgerald et al., "Intravascular Sonotherapy Decreased Neointimal Hyperplasia After Stent Implantation in Swine," Circulation, vol. 103, 2001, pp. 1828-1831.

Freeman et al., "Ultrasonic Aortic Valve Decalcification: Serial Doppler Echocardiographic Follow Up," J Am Coll Cardiol., vol. 16, No. 3, pp. 263-630 (Sep. 1990).

Greenleaf et al., "Selected Methods for Imaging Elastic Properties of Biological Tissues" Annu. Rev. Biomed. Eng., vol. 5, pp. 57-78, (2003).

Gunn et al., "New Developments in Therapeutic Ultrasound-Assisted Coronary Angioplasty," Curr Interv Cardiol Rep., vol. 1 No. 4, pp. 281-290, (Dec. 1990).

Guzman, et al., "Bioeffects Caused by Changes in Acoustic Cavitation Bubble Density and Cell Concentration: A Unified Explanation Based on Cell-To-Bubble Ratio and Blast Radius." Ultrasound in Med. & Biol, vol. 29, No. 8, 2003,1211-1222.

Hallgrmsson et al., "Chronic Non-Rheumatic Aortic Valvular Disease: a Population Study Based on Autopsies," J Chronic Dis.vol. 32 No. 5, 1979, pp. 355-363.

Isner et al., "Contrasting Histoarchitecture of calcified leaflets from stenotic bicuspid versus stenotic tricuspid aortic valves," J Am Coll Cardiol., vol. 15, No. 5, pp. 1104-1108, (Apr. 1990).

(56) References Cited

OTHER PUBLICATIONS

Lung et al., "A Prospective Survey of Patients with Valvular Heart Disease in Europe: The Euro Heart Survey on Valvular Heart Disease," Euro Heart Journal, vol. 24, 2003, pp. 1231-1243.
McBride et al "Aortic Valve Decalcification," J Thorac Cardiovas-Surg, vol. 100, pp. 36-42 (1999).
Miller et al., "Lysis and Sonoporation of Epidermoid and Phagocytic Monolayer Cells by Diagnostic Ultrasound Activation of Contrast Agent Gas Bodies, " Ultrasound in Med. & Biol., vol. 27, No. 8, pp. 1107-1113 (2001).
Mohler, "Mechanisms of Aortic Valve Calcificaion," Am J Cardiol, vol. 94 No. 11, 2004, pp. 1396-1402.
Otto et al., "Three-Year Outcome After Balloon Aortic Valvuloplasty. Insights into Prognosis of Valvular Aortic Stenosis," Circulation, vol. 89, pp. 642-650.
Passik et al., "Temporal Changes in the Causes of Aortic Stenosis: A Surgical Pathologic Study of 646 Cases," Mayo Clin Proc, vol. 62, 1987, pp. 19-123.
Quaden et al., "Percutaneoous Aortic Valve Replacement: Resection Before Implantation," Eur J Cardiothorac Surg, vol. 27, 2005, pp. 836-840.
Riebman et al., "New Concepts in the Management of Patients With Aortic Valve Disease", Abstract, Valvular Heart Disease, JACC, 2004, p. 34A.
Rosenschein et al., "Percutaneous Transluminal Therapy of Occluded Saphenous Vein Grafts," Circulation, vol. 99, 1999, pp. 26-29.
Sakata et al., "Percutaneous Balloon Aortic Valvuloplasty: Antegrade Transseptal vs. Conventional Retrograde Transarterial Approach," Catheter Cardiovasc Interv., vol. 64, 2005, p. 314-321.
Sasaki et al., "Scanning electron microscopy and Fourier transformed infrared spectroscopy analysis of bone removal using Er:YAG and CO2 lasers" J Periodontol.; vol. 73, No. 6, 2002, pp. 643-652.
Search Report and Written Opinion dated May 22, 2007 for PCT Application No. PCT/US2005/044543.
Van Den Brand et al., "Histological Changes in the Aortic Valve after Balloon Dilation: Evidence for a Delayed Healing Process," Br Heart J, 1992; vol. 67, pp. 445-459.
Verdaasdonk et al., "The Mechanism of Action of the Ultrasonic Tissue Resectors Disclosed Using High-Speed and Thermal Imaging Techniques," SPIE , vol. 3594, 1999, pp. 221-231.
Voelker et al., "Inoperative Valvuloplasty in Calcific Aortic Stenosis: a Study Comparing the Mechanism of a Novel Expandable Device with conventional Balloon Dilation," Am Heart J. vol. 122 No. 5, 1999, pp. 1327-1333.
Waller et al., "Catheter Balloon Valvuloplasty of Stenotic Aortic Valves. Part II: Balloon Valvuloplasty During Life Subsequent Tissue Examination," Clin Cardiol., vol. 14 No. 11, 1991, pp. 924-930.
Wang, "Balloon Aortic Valvuloplasty," Prog Cardiovasc Dis., vol. 40, No. 1, 1997, pp. 27-36.
Wilson et al., "Elastography—The movement Begins" Phys. Med. Biol., vol. 45, 2000, pp. 1409-1421.
Yock et al, "Catheter-Based Ultrasound Thrombolysis," Circulation, vol. 95, No. 6, 1997, pp. 1411-1416.
Opposition to European Patent No. EP0930979, Published Jul. 28, 1999, Decision Dated Sep. 12, 2012, 28 pages.
U.S. Appl. No. 95/002,253, Office Action dated Oct. 23, 2013, 24 pages.
U.S. Appl. No. 60/616,254, "Renal neuromodulation", filed Oct. 5, 2004, 25 pages.
U.S. Appl. No. 60/624,793, "Renal neuromodulation", filed Nov. 2, 2004, 20 pages.

\* cited by examiner

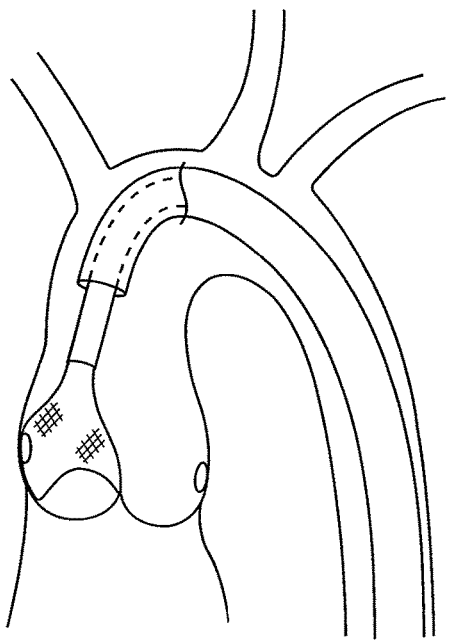
FIG. 65
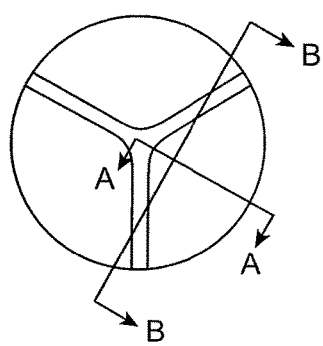 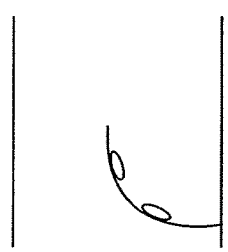 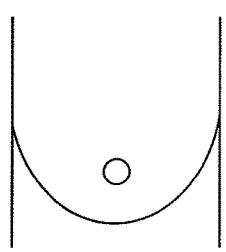
FIG. 66    FIG. 66A    FIG. 66B

INTRAVASCULAR TREATMENT CATHETERS

CROSS-REFERENCE

The present application is a continuation of U.S. patent application Ser. No. 13/692,613, filed Dec. 3, 2012, which is a continuation of U.S. patent application Ser. No. 12/870, 270 filed Aug. 27, 2010, now abandoned, which is a divisional of U.S. patent application Ser. No. 11/299,246 filed Dec. 9, 2005, now U.S. Pat. No. 7,803,168, which claims the benefit of U.S. Provisional Application No. 60/635,275 filed Dec. 9, 2004; U.S. Provisional Application No. 60/662,764 filed Mar. 16, 2005; and U.S. Provisional Application No. 60/698,297 filed on Jul. 11, 2005; the entire contents of these applications are herein incorporated by reference for all purposes.

BACKGROUND OF THE INVENTION

Aortic valve stenosis is a common cardiac disease resulting in approximately 65,000 aortic valve replacement surgeries in the United States annually. Aortic valve stenosis can occur via several etiologies including rheumatic disease, congenital and degenerative calcific stenosis. In developing countries, rheumatic fever results in thickening and progressive immobility of the valve tissues. Calcific disease accounts for almost all of the cases of aortic stenosis in the United States and in developed nations where rheumatic disease is rare.

Over time, a build up of calcium can occur in the annulus of the valve, along the leaflet cusps and on or within the leaflets. This calcific material such as nodular calcific deposits may be superimposed on an underlying fibrotic aortic valve leaflet or calcific deposits may be diffusely distributed throughout the body (spongiosa) of the aortic valve leaflets. Although distribution and type of deposits may differ depending on valve geometry (bicuspid, tricuspid), the deposits generally contribute to leaflet immobility, thickening and other pathologies that lead to degenerative valve function. The presence and progression of this disease leads to a decreased functional area of the valve and dramatically reduced cardiac output.

In the late 1980s and early 1990s balloon dilation of the aortic valve, or valvuloplasty, became a popular therapy for aortic valve stenosis. Dilation of the aortic valve using large angioplasty balloons from either an antegrade (transeptal) or retrograde (aortic) approach resulted in improvements in left ventricular ejection fractions (increased cardiac output), decreases in pressure gradients across the valve, and increases in valve cross-sectional area. Various vavuloplasty balloon designs and other approaches, including energy based therapies, have been disclosed in U.S. Pat. No. 3,667,474 Lapkin, U.S. Pat. No. 4,484,579 Meno, U.S. Pat. No. 4,787,388 Hoffman, U.S. Pat. No. 4,777,951 Cribier, U.S. Pat. Nos. 4,878,495 and 4,796,629 to Grayzel, U.S. Pat. No. 4,819,751 Shimada, U.S. Pat. No. 4,986,830 Owens, U.S. Pat. Nos. 5,443,446 and 5,295,958 to Schturman, U.S. Pat. No. 5,904,679 Clayman, U.S. Pat. Nos. 5,352,199 and 6,746,463 to Tower, the disclosures of which are expressly incorporated herein by reference.

In addition, various surgical approaches to de-calcify the valve lesions were attempted utilizing ultrasonic devices to debride or obliterate the calcific material. Such devices include the CUSA Excel™ Ultrasonic Surgical Aspirator and handpieces (23 kHz and 36 kHz, Radionics, TYCO Healthcare, Mansfield, Mass.). Further work, approaches and results have been documented in "Contrasting Histoarchitecture of calcified leaflets from stenotic bicuspid versus stenotic tricuspid aortic valves," Journal of American College of Cardiology 1990 April; 15(5):1104-8, "Ultrasonic Aortic Valve Decalcification: Serial Doppler Echocardiographic Follow Up" Journal of American College of Cardiology 1990 September; 16(3): 623-30, and "Percutaneous Balloon Aortic Valvuloplasty: Antegrade Transseptal vs. Conventional Retrograde Transarterial Approach" Catheterization and Cardiovascular inverventions 64:314-321 (2005), the disclosures of which are expressly incorporated by reference herein.

Devices and techniques have suffered from only a modest ability to increase valve cross-sectional area, however. For instance, many studies showed that a pre-dilatation area of about 0.6 $cm^2$ could be opened to only between about 0.9 to about 1.0 $cm^2$. It would be desirable to open such a stenosis to an area closer to about 1.2 to about 1.5 $cm^2$. In addition to opening the cross-sectional area, it may be desirable to treat the leaflets and surrounding annulus to remove calcific deposits that stiffen the valve, impair flow dynamics, and otherwise degenerate valve function. Toward this end, other techniques such as direct surgical ultrasonic debridement of calcium deposits have had some success, but required an open surgical incision, thereby increasing the risk to the patient.

Although balloon dilatation offered patients a viable, less invasive alternative, it fell into disfavor in the early to mid 1990s primarily as a result of rapid restenosis of the valve post treatment. At six months, reports of restenosis rates were commonly in excess of 70-80%. Today, balloon valvuloplasty is primarily reserved for palliative care in elderly patients who are not candidates for surgical replacement due to comorbid conditions.

Recent clinical focus on technologies to place percutaneous valve replacement technologies have also caused some to revisit valvuloplasty and aortic valve repair. Corazon, Inc. is developing a system which isolates the leaflets of the aortic valve so that blood flow through the center of the device is preserved while calcium dissolving or softening agents are circulated over and around the leaflets. See for example, United States Patent Application Publication 2004/0082910, the disclosure of which is expressly incorporated herein by reference. The hope is that reducing the stiffness of the leaflets by softening the calcium will allow for more normal functioning of the valve and increased cardiac output. The system is complex, requires upwards of 30 minutes of softening agent exposure time, and has resulted in complete AV block and emergency pacemaker implantation in some patients.

In addition, other technologies have been documented to address aortic stenosis in various ways. U.S. Patent Application Publication 2005/007219 to Pederson discloses balloon materials and designs, as well as ring implants for use in vavuloplasty and treatment of aortic stenosis, the disclosure of which is expressly incorporated herein by reference. Further, Dr. Pederson recently presented initial results of the RADAR study for aortic valve stenosis therapy. This study combines traditional balloon valvuloplasty with external beam radiation to try to prevent the restenosis which occurs post-dilatation. While radiation therapy has been shown to have a positive impact on restenosis in coronary angioplasty, the methods employed in the RADAR study require that the patient undergo a minimum of 4-6 separate procedures, the initial valvuloplasty plus 3-5 separate radiation therapy sessions. These radiation therapy sessions are similar to those used for radiation treatment for cancer.

Over the past three years, dramatic advances in the prevention of restenosis after coronary balloon angioplasty and stenting have been made by the introduction of drug-eluting stents by companies like Boston Scientific and Johnson & Johnson. These devices deliver a controlled and prolonged dose of antiproliferative agents to the wall of the coronary artery in order to manage the sub-acute wound healing and prevent the long-term hyperproliferative healing response that caused restenosis in bare metal stents or in stand-alone angioplasty. Furthermore, various advances have been made on the administration of anti-calcification drugs, including ACE inhibitors, statins, and angiotensins, specifically angiotensin II, as detailed in United States Patent Application Publication 2004/0057955, the disclosure of which is expressly incorporated herein by reference.

While the conventional methods have proven to be reasonably successful, the problem of aortic valve stenosis and subsequent restenosis after valvuloplasty or other intervention still requires better solutions. The present invention provides various devices and methods that create more effective treatments for aortic stenosis and prevent or reduce the incidence and/or severity of aortic restenosis. In addition, the present inventions provides methods and devices for decalcification or debridement of aortic stenosis, either as a stand alone therapy or in conjunction with conventional techniques, such as traditional valvuloplasty, stenting, valve repair, and percutaneous or surgical valve replacement.

SUMMARY OF THE INVENTION

The present invention relates to the repair of aortic and other cardiac valves, and more particularly devices and methods for calcium removal and anti-restenosis systems for achieving such repair. The invention can take a number of different forms, including apparatus, acute interventions performed at the time of the aortic repair or valvuloplasty, or temporary or permanent implant, and the like.

In one aspect, the methods and devices of the reduce or remove calcifications on or around the valve through application or removal of energy to disrupt the calcifications. The present invention may apply ultrasound energy, RF energy, a mechanical energy, or the like, to the valve to remove the calcification from the valve. Alternatively, it may be desirable to instead remove energy (e.g. cryogenically cooling) from the calcification to enhance the removal of the calcification from the valve. In all cases, it will be desirable to create an embolic containment region over a localized calcific site on or near the cardiac valve. Such containment may be achieved by creating a structure about the localized site and/or by actively aspirating embolic particles from the site as they are created. Suitable structures include filters, baskets, balloons, housings and the like.

In another aspect of the present invention, treatment catheters are provided to deliver a working element to the vicinity of the diseased valve. Working element can include an ultrasonic element, or any other delivery mechanism or element that is capable of disrupting, e.g., breaking up or obliterating calcific deposits in and around the cardiac valve. Such devices may be steerable or otherwise positionable to allow the user to direct the distal end of the catheter grossly for initial placement through the patient's arteries to the valve, and then precisely adjust placement prior to and/or during treatment.

In another aspect, the present invention provides a treatment catheter that comprises a mechanical element that can disrupt, e.g., mechanically break up, obliterate, and remove the calcific deposits in and around the aortic valve. Similar to the ultrasonic-based catheters, the catheter comprising the mechanical element may be steerable or otherwise articulable to allow the user to direct the distal end of the catheter grossly for initial placement, and then fine tune placement during treatment.

In a further aspect of the present invention, systems including a guide catheter may also be employed to position the treatment catheter at the site of the disease to be treated, either as a separate catheter or as part of the treatment device. In one embodiment, a main guide catheter may be used to center a secondary positioning catheter that contains the treatment catheter over the aortic valve. The treatment catheter may then be further articulated to provide even further directionality to the working end. Various other apparatus and methods may be employed for positioning and stabilizing the treatment catheter, including shaped balloons, baskets or filters and methods of pacing the heart.

In a further aspect of the present invention, methods may be used to disrupt the calcified sites and trap and evacuate emboli and other debris from the treatment site, using filters located on the treatment catheter, suction housings located on the treatment catheter, perfusion balloons linked with aspiration devices, separate suction catheters, separate filter devices either at the treatment site or downstream from the treatment site, and/or external filter and perfusion systems. Certain filter embodiments may be shaped to allow the treatment catheter to access the location to be treated, while still allowing flow through the valve (e.g. treating one leaflet at a time).

In particular, methods for treating cardiac valves according to the present invention comprise creating an emboli containment region over a calcific site and delivering energy (including cryotherapy) to disrupt said site and potentially create emboli which are contained in the containment region. The containment regions will typically be localized directly over a target site, usually having a limited size so that the associated aorta or other blood vessel is not blocked or occluded. The containment region may be created using a barrier, such as a filter structure, basket, or balloon over the calcified site. Alternatively or additionally, the containment region may be created by localized aspiration to remove substantially all emboli as they are formed. The energy applied may be ultrasound, radiofrequency, microwave, mechanical, cryogenic, or any other type of energy capable of disrupting valve calcifications.

In a further aspect of the present invention, the methods may virtually disintegrate the calcification through the use a media that contains microspheres or microbubbles, such as Optison™ sold by GE Healthcare (www.amershamhealth-us.com/optison/). Delivery of an ultrasound energy (or other form of energy, for example, laser, RF, thermal, energy) to the media may cause the microspheres to rupture, which causes a release of energy toward the valve, which may help remove the calcification around and on the valve. *Bioeffects Caused by Changes in Ascoustic Cavitation Bubble Density and Cell Concentration: A Unifed Explanation Based on Cell-to-Bubble Ratio and Blast Radius*, Guzman, et al. Ultrasound in Med. & Biol., Vol. 29, No. 8, pp. 1211-1222 (2003).

Certain imaging and other monitoring modalities may be employed prior to, during or after the procedure of the present invention, utilizing a variety of techniques, such as intracardiac echocardiography (ICE), transesophageal echocardiography (TEE), fluoroscopy, intravascular ultrasound, angioscopy or systems which use infrared technology to "see through blood", such as that under development by Cardio-Optics, Inc.

Various energy sources may be utilized to effect the treatment of the present invention, including RF, ultrasonic energy in various therapeutic ranges, and mechanical (non-ultrasound) energy. The distal tips of the RF, ultrasonic treatment catheters, and mechanical treatment catheters of the present invention may have a variety of distal tip configurations, and be may be used in a variety of treatment patterns, and to target specific locations within the valve.

In addition, intravascular implants are contemplated by the present invention, including those placed within the valve annulus, supra annular, sub annular, or a combination thereof to assist in maintaining a functional valve orifice. Such implants may incorporate various pharamacological agents to increase efficacy by reducing restenosis, and otherwise aiding valve function. Implants may be formed of various metals, biodegradable materials, or combinations thereof.

These devices may all be introduced via either the retrograde approach, from the femoral artery, into the aorta and across the valve from the ascending aorta, or through the antegrade approach—transeptal, across the mitral valve, through the left ventricle and across the aortic valve.

In other aspects, the present invention provides an anti-restenosis system for aortic valve repair. Acute interventions are performed at the time of the aortic repair or valvuloplasty and may take the form of a temporary or permanent implant.

These implant devices may all be introduced via either the retrograde approach, from the femoral artery, into the aorta and across the valve from the ascending aorta, or through the antegrade approach—trans-septal, across the mitral valve, through the left ventricle and across the aortic valve, and will provide for delivery of anti-restenosis agents or energy to inhibit and/or repair valve restenosis.

BRIEF DESCRIPTION OF THE DRAWINGS

FIG. 65 shows a filter shape optimized for a leaflet at the treatment site.

FIGS. 66-68 show catheter positions optimized for reducing calcium deposits.

DETAILED DESCRIPTION OF THE INVENTION

Treatment Catheter Design—General

Figure 1:
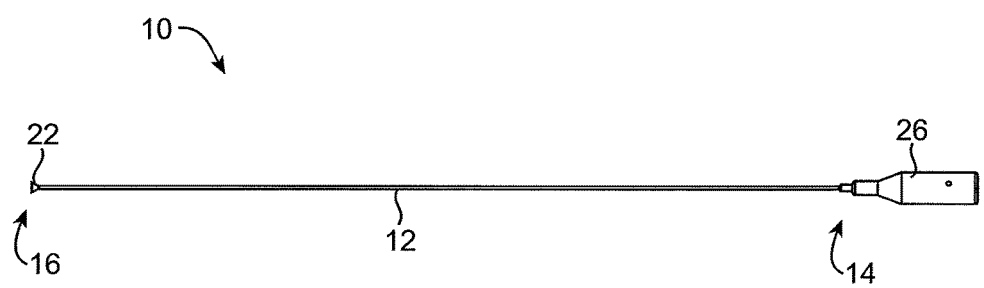
FIG. 1 illustrates a suction catheter constructed in accordance with the principles of the present invention.

Treatment catheters 10 (FIG. 1) of the present invention typically comprise an elongate catheter body 12 that comprises a proximal end 14, a distal end 16, and one or more lumens 18, 20 (FIG. 2) within the catheter body. The distal end 16 may optionally comprise a suction housing 22 (FIGS. 4 and 5) that extends distally from the distal end of the catheter body 12 for isolating the leaflet during treatment as well as providing a debris evacuation path during treatment and protecting the vasculature from adverse embolic events. An energy transmission element 24 (e.g., a drive shaft, wire leads, or a waveguide-ultrasonic transmission element, or the like) may be positioned in one of the lumens in the elongate body 12 and will typically extend from the proximal end to the distal end of the catheter body. A handle 26 is coupled to the proximal end 14 of the elongate catheter body 12. A generator (e.g., RF generator, ultrasound generator, motor, optical energy source, etc.) may be coupled to the handle to deliver energy to a distal waking end 28, the energy transmission element 24 that is disposed within a lumen of the catheter body. As described herein, the distal working element 28 may be coupled to the distal end of the energy transmission element 24 to facilitate delivery of the energy to the calcification on the aortic valve.

Figure 2:
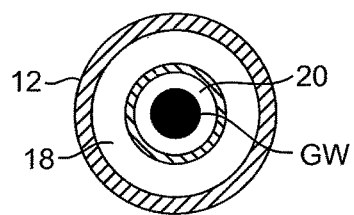
FIG. 2 is a cross-sectional view of the catheter of FIG. 1.
Figure 3:
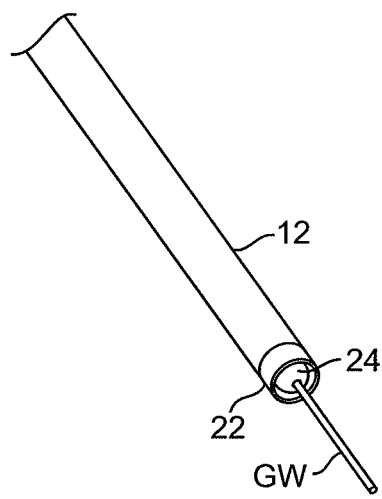
FIGS. 3 and 4 are detailed views of the distal end of the catheter of FIG. 1, with FIG. 4 showing a suction housing in an expanded configuration.

Typically, the treatment catheters 10 of the present invention are configured to be introduced to the target area "over the wire." The treatment catheters may be positioned adjacent the aortic valve through a guide catheter or sheath. As such, the treatment catheters of the present invention may comprise a central guidewire lumen 20 for receiving a guidewire GW (FIG. 2). The guidewire lumen 20 of the treatment catheters of the present invention may also be used for irrigating or aspirating the target area. For example, while not shown, the handle may comprise one or more ports so as to allow for irrigation of the target leaflet and/or aspiration of the target area. An irrigation source and/or an aspiration source may be coupled to the port(s), and the target area may be aspirated through one of the lumen of the catheter and/or irrigated through one of the lumens of the catheter. In one embodiment, one of the irrigation source and aspiration source may be coupled to the central guidewire lumen (central lumen) and the other of the aspiration source and the irrigation source may be coupled to the lumen that is coaxial to the guidewire lumen. In some embodiments, however, there will be no inner guidewire lumen and the guidewire will simply extend through the ultrasound waveguide and the rotatable drive shaft, as shown in FIGS. 3, 4 and 6.

As noted above, the treatment catheters 10 of the present invention may comprise a suction housing positioned at the distal end of the catheter body having an expanded configuration and a retracted configuration and configured to conform to the valve leaflet to be treated. While the suction housing 22 may be fixedly attached at the distal end, in preferred embodiments, the suction housing is movable between a retracted configuration (FIG. 3) and an expanded configuration (FIGS. 4 and 5). A separate sheath may also be retracted to expose the suction housing and advanced to fold the housing. The suction housing may be made from silicone or urethane and may be reinforced with an internal frame or mesh reinforcement to provide structural support or to enhance placement of the housing on a specified area of the valve leaflet. The housing may further act as an embolic filter as detailed later in this specification.

Figure 4:
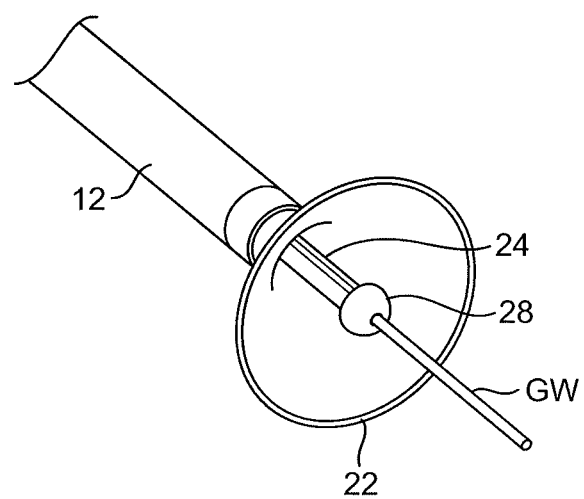
Figure 5:
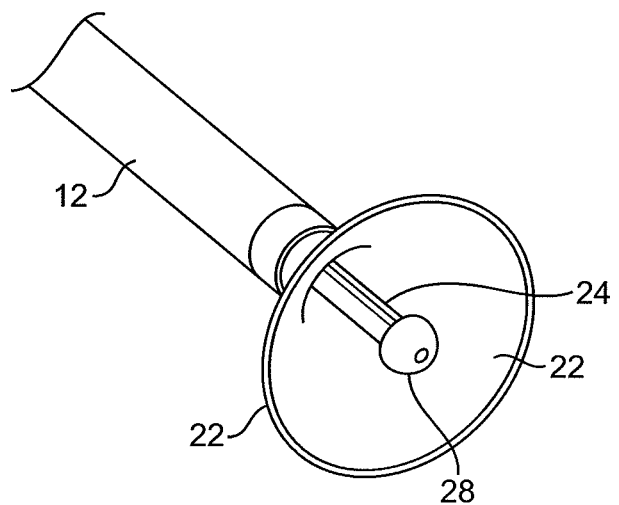
FIG. 5 is similar to FIG. 4, showing the catheter without a guidewire.

In the embodiment of FIG. 4, the energy transmission element 24 is advanced beyond the distal end of the catheter body 12 and into the suction housing 22. The guidewire GW is positioned through an opening in the distal tip. As in FIG. 5, once the treatment catheter is positioned at the target area, the guidewire GW is withdrawn and the distal working element 28 is ready for use to treat the calcification.

Figure 6:
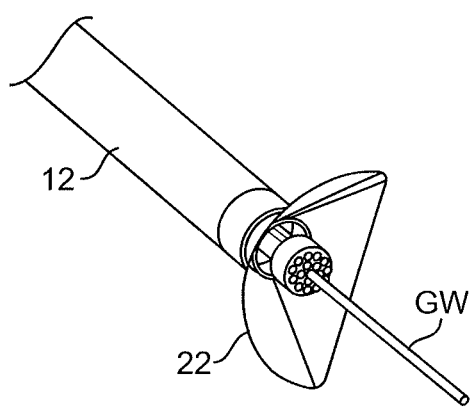
FIGS. 6-8 show modified suction housings.
Figure 7:
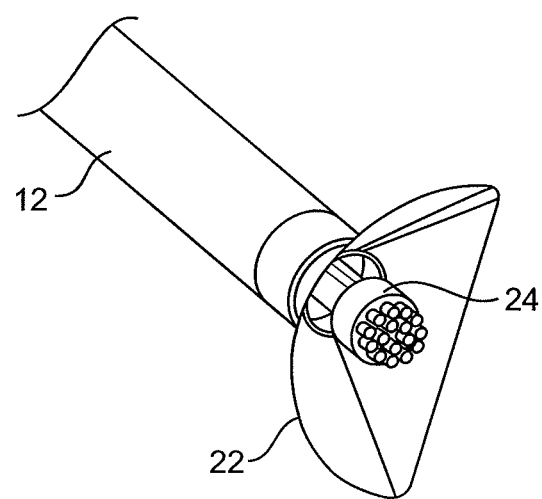
Figure 8:
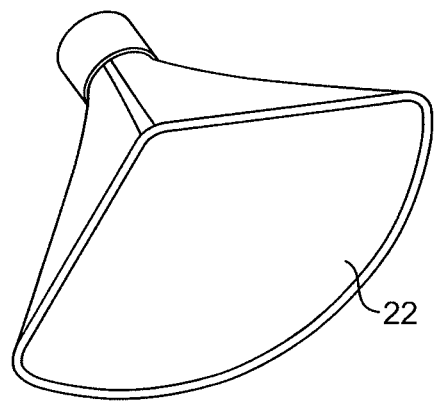

In FIG. 6, the suction housing 22 is shaped to substantially conform to the shape of a bicuspid valve leaflet. By shaping the suction housing to conform to the shape of the leaflet, the suction housing may be better configured to isolate the target leaflet. In other embodiments, the suction housing may be shaped to substantially conform to a tricuspid valve (FIGS. 7 and 8), etc.

Figure 9:
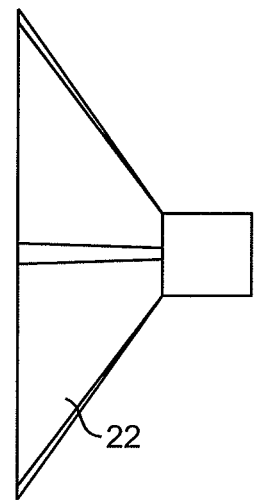
FIGS. 9 and 10 show suction housings having different depths.
Figure 10:
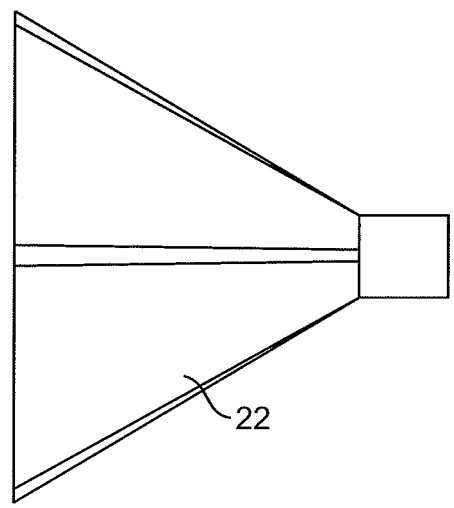

The depth of the suction housing may take many forms such that it is compatible with the valve to be treated. For example, the suction housing 22 may be shallow (FIG. 9) or deep (FIG. 10). The depth on the cup can reduce or eliminate obstructing the coronary ostia if one of the leaflets under treatment is a coronary leaflet.

Figure 11:
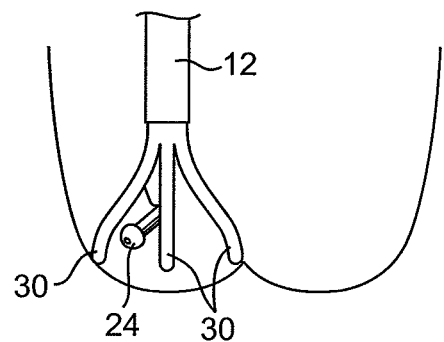
FIGS. 11-13 show suction housings having rigid or semi-rigid members around their circumferences.
Figure 12:
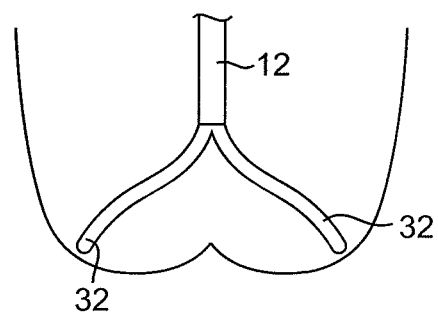
Figure 13:
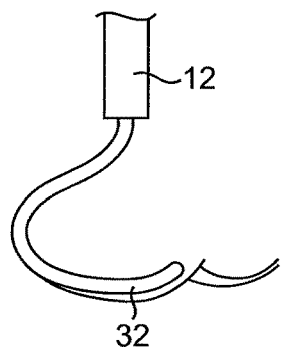

The suction cups/housings may also have rigid or semi-rigid members around the circumference or part of the circumference of the housing to preferentially align the cup on certain valve features, such as the annulus. The suction cup housings have a depth range of 0.1" to 0.5" and a diameter of 15 mm to 30 mm. The cup or housing may have fingers 30 or longitudinal stabilizing elements 32 to assist in placing the housing against the valve as shown in FIGS. 11, 12, and 13.

Such stabilizing elements may also be in the form of pleats, rings or hemispherical elements, or other reinforcements to assist the device to seat within the annulus of the valve or against the leaflet. Such reinforcements or stabilizing elements may be formed of stainless steel, NiTi (superelastic or shape memory treated), Elgiloy®, cobalt chromium, various polymers, or may be in the form of an inflatable ringed cup. The cup or housing of the present invention is intended to function to provide sufficient approximation with the treatment area so as to stabilize or localize the working element while also minimizing embolic events. It that sense, it is substantially sealing against the treatment region, but such seal is not necessarily an "airtight" seal, but an approximation that performs the desired functions listed above.

Figure 14:
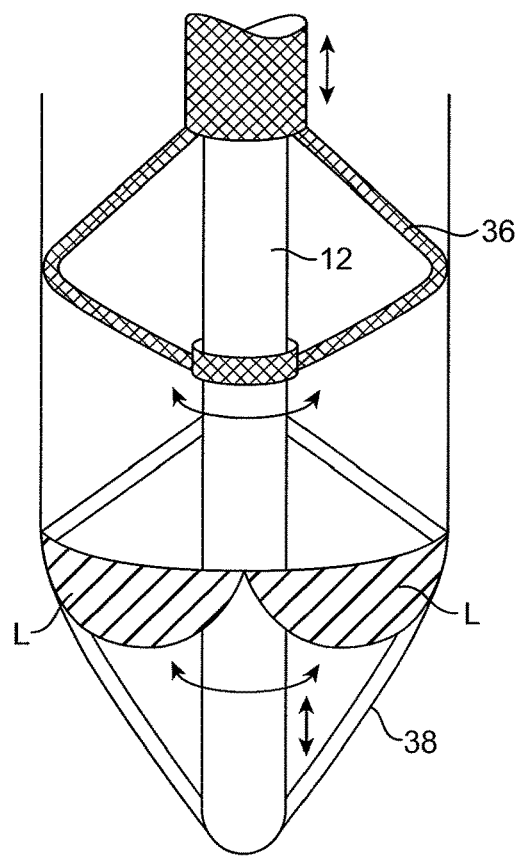
FIG. 14 shows a suction catheter having a stabilizing structure near its distal end.

In addition, certain stabilizing devices 36, 38 may be located on the main catheter shaft 12 to provide stability within the aorta, and may, in some cases, extend through the valve leaflets L below the valve to further stabilize the treatment device, as shown in FIG. 14.

Figure 15:
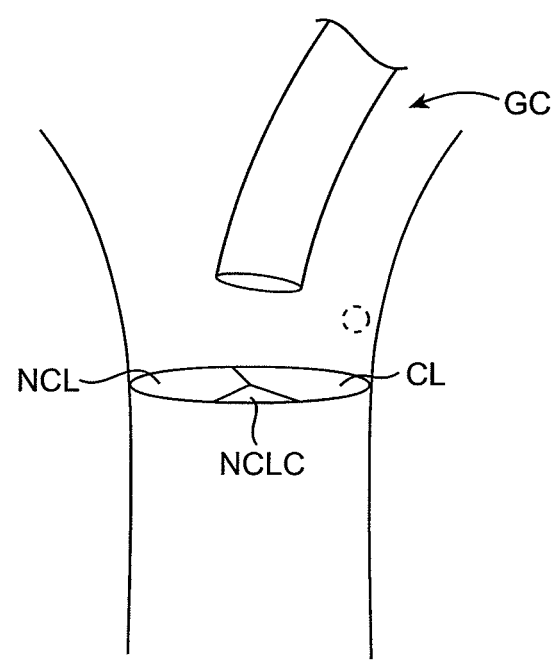
FIG. 15 illustrates how a guiding catheter would be used to place the catheters of the present invention above a treatment area.
Figure 16:
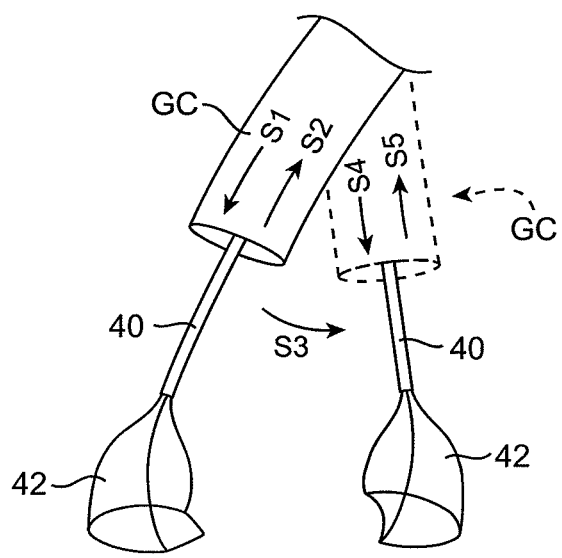
FIGS. 16 and 17 show how suction catheters would be placed through the guide catheters.
Figure 17:
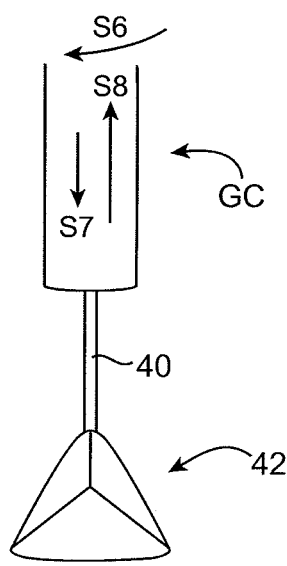
Figure 18:
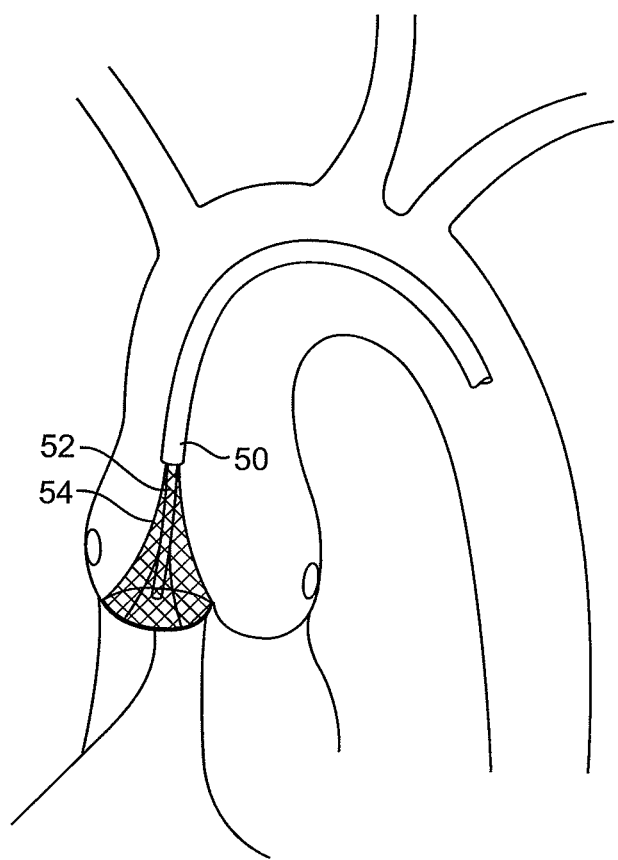
FIGS. 18-22 illustrate the use of treatment catheters having ultrasonic probes for decalcifying leaflets in accordance with the principles of the present invention.

Given the variety of leaflet geometries (e.g. size, curvature) from leaflet to leaflet, and patient to patient, it may be desirable to provide a main treatment catheter through which a variety of sized and shaped cups or housings can be passed, depending on the particular geometry to be treated. For example, a system could include a main guide catheter GC placed over the treatment area as depicted in FIG. 15: The treatment area (leaflets) include the coronary leaflet (CL), the non-coronary leaflet (NCL) and the non-coronary leaflet (center) (NCLC). As shown below in FIG. 16, once the guide catheter GC is in place a first treatment catheter 40 having a distal housing 42 adapted to conform to the NCL is advanced as indicated by arrow S1. The leaflet is treated and the NCL housing catheter is withdrawn as indicated by S2. The guide catheter position is then adjusted as indicated by arrow S3 to better approximate the CL. CL housing catheter is the advanced through the guide as indicated by arrow S4. Once the CL position is treated, the CL housing catheter is removed as indicated by arrow S5. As further depicted in FIG. 17, the guide catheter GC is then repositioned to treat NCLC as indicated by arrow S6, and finally the NCLC housing catheter is advanced through the guide according to arrow S7. Once the treatment is complete, the NCLC is removed as indicated by arrow S8 and the guide is removed and procedure completed.

It is within the scope of the present invention to use any one of these steps, in any order to treat the targeted region, for example, one leaflet may be treated only, more than one leaflet, and in any order according to the type of calcification, health of the patient, geometry of the target region or preference of the operator.

Ultrasound Treatment Catheters

Figure 19:
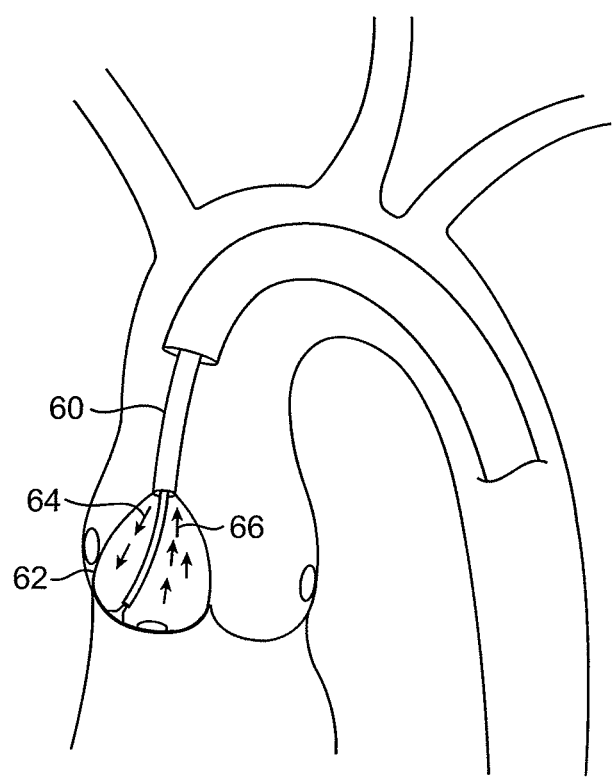

In accordance with one aspect of the present invention a treatment catheter 50 is provided having an ultrasonic probe for decalcifying the leaflet. An ultrasonic probe 52 may be surrounded by a frame or sheath 54. Both the frame and the sheath may be connected to a source of ultrasonic vibration (not shown). In certain embodiments, the probe 52 is surrounded by a sheath or housing that enables the system to be substantially sealed against the treatment surface via a source of suction attached at the proximal end of the catheter system and connected to the catheter housing via a suction lumen in the catheter body. Alternatively, the system may be placed or localized at the treatment site with a mechanical clip or interface that physically attaches the housing to the treatment area (annulus or leaflet). In operation, the ultrasonic probe 52 is activated to disintegrate the calcium on the leaflets, creating debris that may then be removed through a suction lumen in the catheter body 50. In some cases it may be desirable to also infuse saline or other fluids into the housing area simultaneously or prior to application of suction. It may be advantageous to provide a cooling fluid to the ultrasonic waveguide as well and to other embodiments such as one with a PZT stack at the distal end of the device. It may also be advantageous to infuse anti-calcification therapy to the site of the valve, including a ferric and/or stannic salt, or other solution as in known in the art to tan or otherwise make the leaflets resistant to calcium buildup, such as the type set forth in U.S. Pat. No. 5,782,931, the contents of which is expressly incorporated by reference herein. Another embodiment of an ultrasonic probe 60 having a silicone cup is shown in FIG. 19 where infusate is indicated by arrows 62 and aspirate is indicated by arrows 64.

Figure 20:
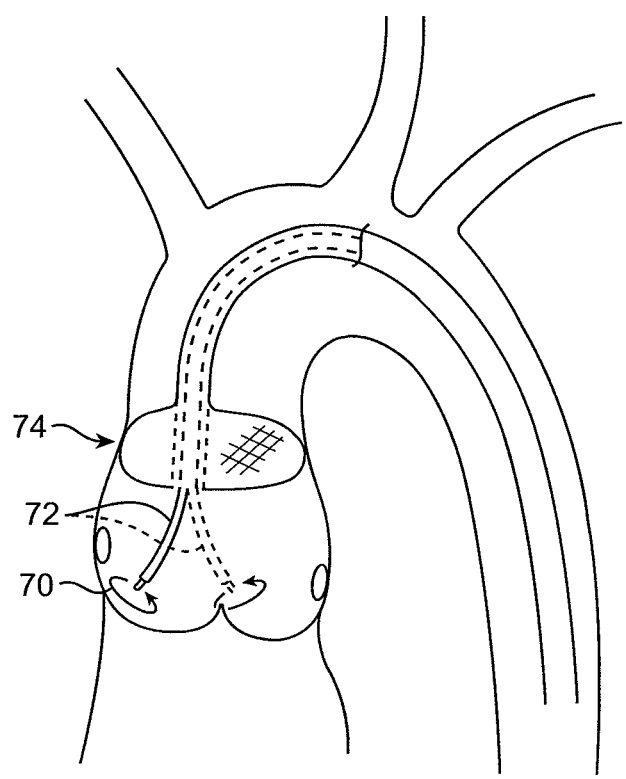

In embodiments where a filter device 74 is disposed on the main catheter shaft (shown in FIG. 20), the ultrasonic probe 70 may be a separate element, allowing the ultrasonic treatment catheter 72 to move independently within the sealed region. The treatment probe 70 may be operated in a variety of directions and patterns that are further detailed in the specification, including sweeping in a circular pattern along the cusp of each leaflet and creating concentric circles during treatment to effectively treat the entire leaflet, if necessary. In the absence of a filter device, the ultrasonic element may be coaxial with the suction housing and adapted to move independently therewithin.

Figure 21:
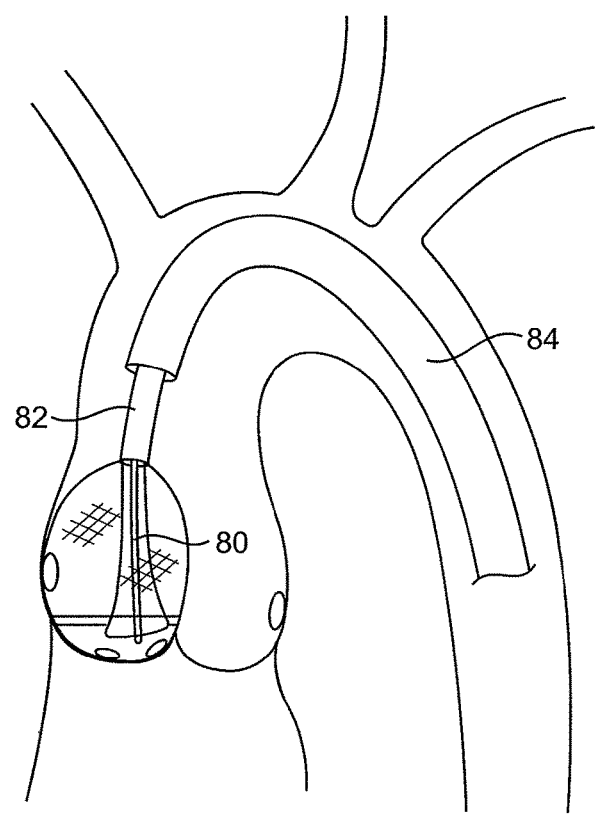
Figure 22:
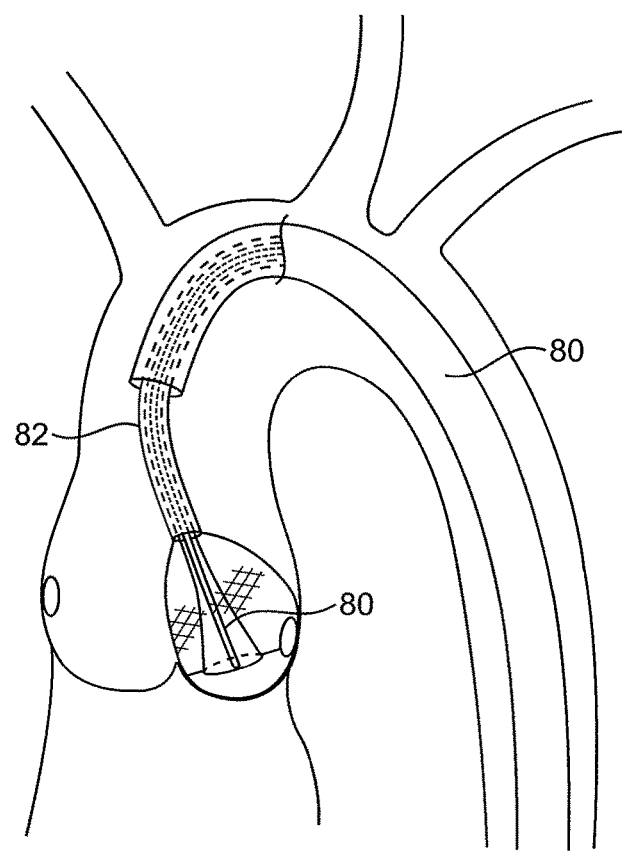

As shown in FIG. 21, in accordance with another aspect of the present invention, a treatment catheter 80 may be placed through a series of guide catheters 82, 84 to assist placement accuracy. The first guide member 84 may be placed and anchored in the aortic root using either the shape of the guide to anchor against the aortic wall, or a separate balloon or filter device to stabilize the guide or a stabilizing ring made from shape memory material or other suitable material that can provide stabilization to allow the catheter to be directed to the treatment site. A second steerable or articulable catheter 82 may then be placed through the initial guide to direct the treatment catheter to one area of the leaflet or other. The treatment catheter 80 may then be placed through the system once these guides are in place, and deployed directly to the targeted valve region. In the case of a method that treats one leaflet at a time, the steerable guide may then be actuated to target the next treatment location, thereby directing the treatment catheter (and related filtering devices) to the next site. It may only be necessary to place one guide catheter prior to the treatment catheter, or alternatively, the treatment catheter may be steerable, allowing it to be placed directly to the treatment site without the aid of other guide catheters. The guide catheter may also be steerable and an integral part of the treatment catheter. Steerable guides such as those depicted in US Patent Publications 2004/0092962 and 2004/0044350 are examples, the contents of which is expressly incorporated by reference in its entirety. Treatment device may then be re-directed to a second treatment site, as shown in FIG. 22.

Figure 23:
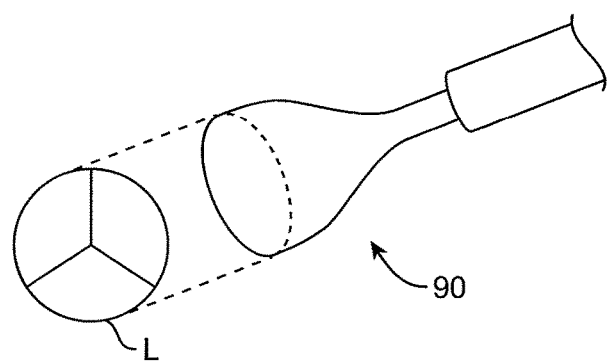
FIG. 23 illustrates a catheter having a distal portion shaped to correspond to a shape of a targeted valve leaflet.

The distal portion 90 of the treatment catheters of the present invention may be shaped to substantially correspond to a shape of the targeted leaflet L (e.g., formed to fit within shape of the leaflet cusp, with the mouth of the housing being shaped to conform to the leaflet shape as shown in FIG. 23). This also enables the surface of the leaflet to be stabilized for treatment. The distal portion may have an internal frame that supports the distal section during deployment and treatment but is flexible such that it collapses into the treatment catheter or sheath to assist with withdrawal.

Figure 24:
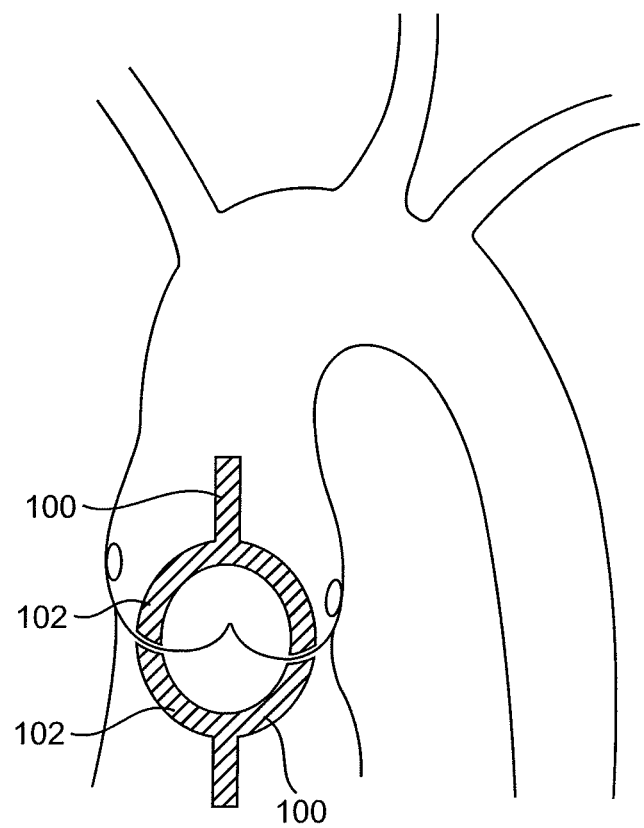
FIG. 24 illustrates a catheter having a distal end with an annular treatment surface adapted to apply energy to a valve annulus.

Alternatively, the treatment catheter 100 of the present invention may be formed having a circumferential, annular treatment 102 surface to apply energy/vibration to the annulus to be treated. In this embodiment the catheter may be placed antegrade or retrograde, or two circumferential treatment surfaces may be used in conjunction with each other, as shown in FIG. 24.

Figure 25A:
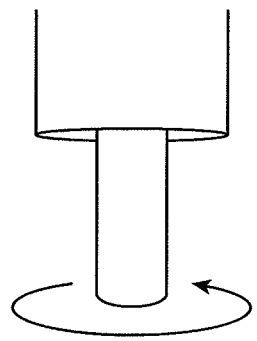
FIGS. 25A-25D illustrate catheters having different working ends in accordance with the principles of the present invention.
Figure 25B:
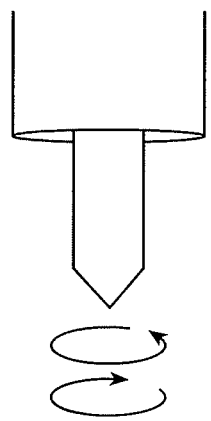
Figure 25C:
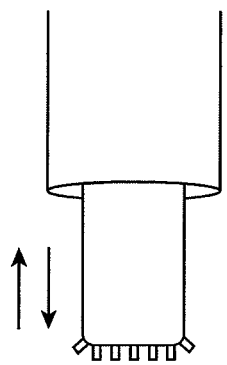
Figure 25D:
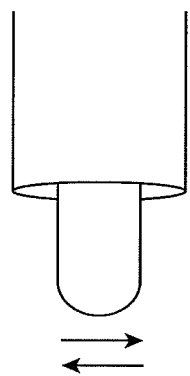

Various ultrasonic working ends may be used, depending on the type and location of the disease to be treated. For example, the distal tip of an ultrasonic catheter may be coupled to a ultrasound transmission member or waveguide. The distal tip may be chosen from the various examples below, including a blunt tip, a beveled tip, a rounded tip, a pointed tip and may further include nodules or ribs (FIG. 25C) that protrude from the surface of the tip to enhance breakup of calcium. Arrows show exemplary patterns of use.

The distal tip of the ultrasonic catheters of the present invention may also take the shape of the waveguide tips that are shown and described in U.S. Pat. No. 5,304,115, the contents of which is expressly incorporated by reference herein. U.S. Pat. No. 5,989,208 ("Nita"), the contents of which is expressly incorporated by reference herein, illustrate some additional tips in FIGS. 2-7A that may also be useful for decalcifying a valve leaflet.

Figure 26:
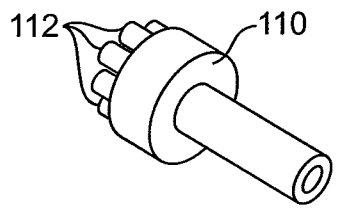
FIGS. 26-28 illustrate catheters having ultrasonic transmission members and enlarged working ends.
Figure 27:
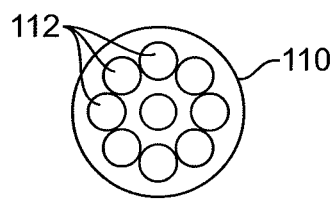
Figure 28:
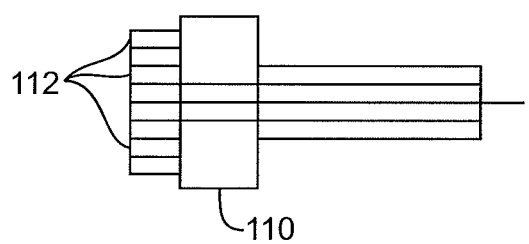

The ultrasound transmission members of the present invention may comprise a solid tube that is coupled to an enlarged distal working end. A central lumen may extend throughout the ultrasonic transmission member and may be used for aspiration, suction, and/or to receive a guidewire. In the embodiment illustrated in FIGS. 26, 27 and 28, the enlarged working end 110 (which has a larger diameter than the elongate proximal portion), may comprise a cylindrical portion that comprises a plurality of elongated members 112. In the illustrated configuration, the elongated members are arranged in castellated pattern (e.g., a circular pattern in which each of the elongated members extend distally) and provide an opening along the longitudinal axis of the ultrasound transmission member. While the elongated members are cylindrically shaped, in other embodiments, the elongated members may be rounded, sharpened, or the like.

Figure 29:
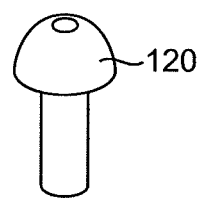
FIGS. 29-31 illustrate catheters having enlarged distal working ends with central lumens therethrough.
Figure 30:
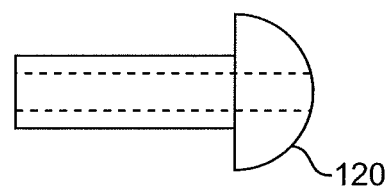
Figure 31:
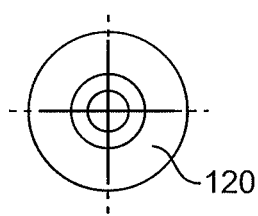

In a further embodiment of the distal working end, similar to the embodiment illustrated above, a central lumen may extend through the ultrasound transmission element and through the enlarged distal working end. In the configuration illustrated in FIGS. 29, 30 and 31, the distal working end 120 is enlarged and rounded.

Figure 32:
FIGS. 32 and 33 illustrate catheters having ultrasonic transmission elements adjacent a working end.
Figure 33:
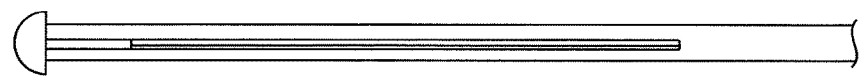
Figure 34:
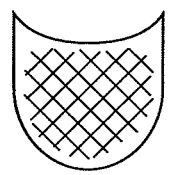
FIGS. 34-37 illustrate different patterns of motion which may be imparted by the electronic catheters of the present invention.
Figure 35:
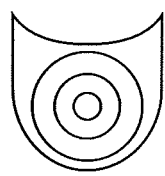

In alternative embodiments, the portion of the ultrasound transmission element (or waveguide) that is adjacent the distal working end may be modified to amplify the delivery of the ultrasonic waves from the working end. The waveguide may comprises a plurality of axial slots in the tubing that act to create a plurality of "thin wires" from the tubing, which will cause the ultrasonic waves to move radially, rather than axially. The enlarged distal working end may then be attached to the plurality of thin wires. Two embodiments of such a configuration are illustrated in FIGS. 32 and 33. In an alternative embodiment, each castellation may be housed on its own shaft extending back to the proximal end of the device. Other potential tip geometries are depicted below.

Figure 36:
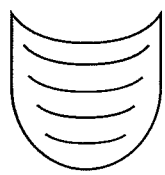
Figure 37:
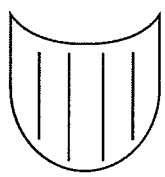

The ultrasonic catheters of the present invention may be adapted to impart motion to the distal tip that is oscillatory, dottering, circular, lateral or any combination thereof. For any of such distal tips described herein, Applicants have found that the use of a small distal tip relative to the inner diameter of the catheter body provides a better amplitude of motion and may provide improved decalcification. In addition, an ultrasonic tip of the present invention can be operated in a variety of treatment patterns, depending on the region of the leaflet or annulus that is being treated, among other things. For example, the treatment pattern, either controlled by the user programmed into the treatment device, may be a circular motion to provide rings of decalcification on the surface being treated, a cross-hatching pattern to break up larger deposits of calcium (FIG. 24), or a hemispherical (FIG. 36) or wedge-shaped (FIG. 37) pattern when one leaflet or region is treated at a time. It is within the scope of the present invention to use combinations of any of the patterns listed, or to employ more random patterns, or simply a linear motion.

Figure 38:
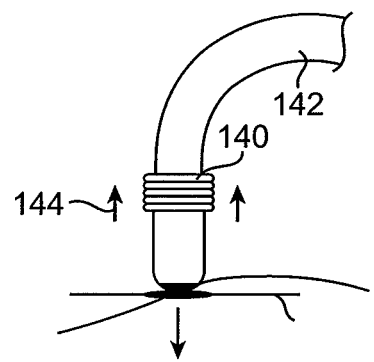
FIG. 38 illustrates a catheter having a force limiting feature.

Certain safety mechanisms may be incorporated on the treatment catheter and related components to ensure that the treatment device does not perforate or otherwise degrade the leaflet. In one embodiment, a force limiting feature may be incorporated into the treatment catheter shaft as shown in FIG. 38, where a structure 140 can contract in response to force applied to catheter 142 in the direction of arrows 144.

Figure 39:
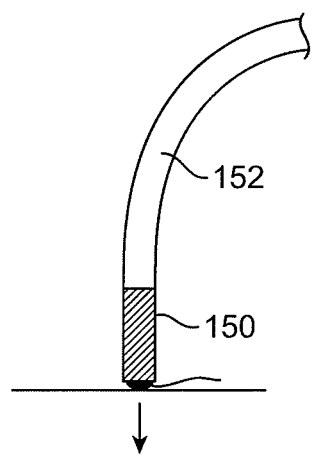
FIGS. 39 and 40 illustrate a catheter having a deflectable distal end.
Figure 40:
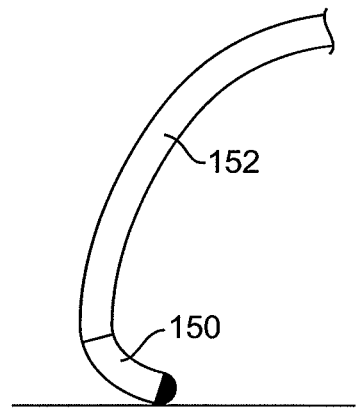

In another embodiment, features of the catheter shaft may limit the force that is delivered to the tissues. A soft distal tip 150 (FIG. 39) on a relatively rigid catheter shaft 152, where the forces can deflect the tip, as shown in FIG. 40.

Figure 41:
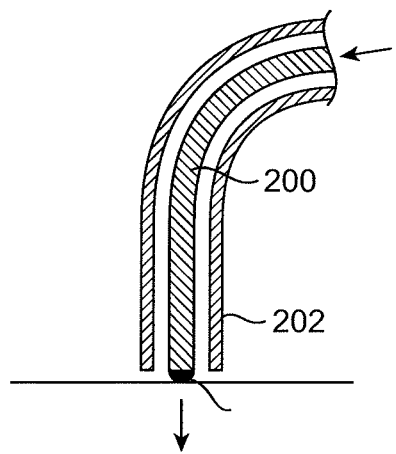
FIGS. 41 and 42 illustrate treatment catheters being advanced through a sheath.
Figure 42:
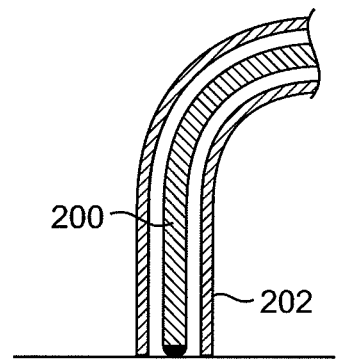

In addition, the treatment catheter 200 may be advanced through a sheath 202 that acts as a depth limiter to the treatment catheter as shown in FIGS. 41 and 42. These various safety features may be incorporated into any of the treatment devices of the present invention, regardless of the energy employed.

Figure 43:
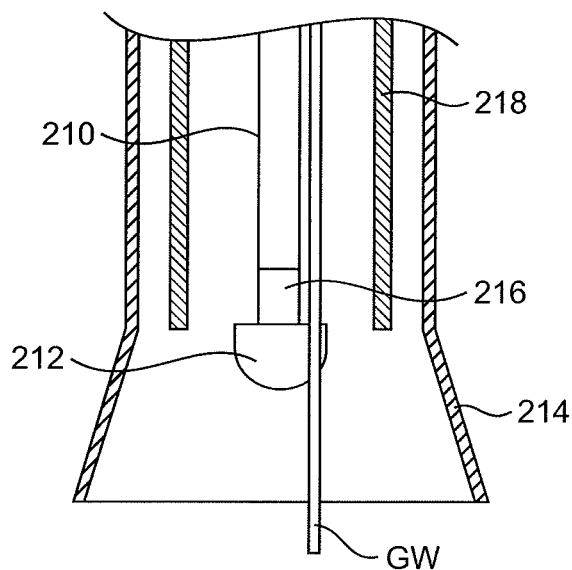
FIG. 43 illustrates an ultrasonic catheter having a distal horn and a PZT stack.

An assembly of an ultrasonic catheter of the present invention is shown in FIG. 43, including an ultrasonic transmission member 210, a transmission-head 212, a guide wire GW, a suction cup 214, a spring 216, and catheter body 218.

Figure 44:
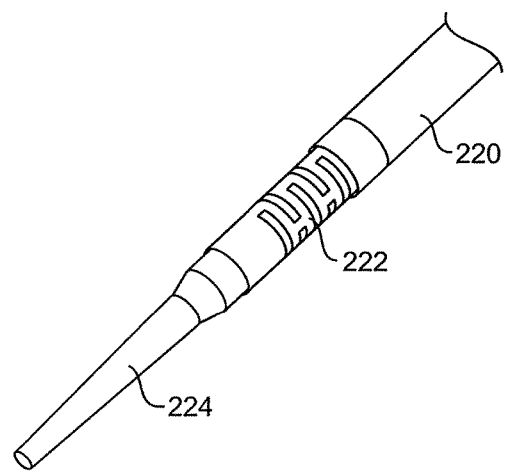
FIG. 44 illustrates a suction housing placed over a PZT stack and ultrasonic horn in an embodiment of the present invention.

Another embodiment of an ultrasonic catheter 220 includes a PZT stack 222 and a distal horn 224 at the distal end of the device as shown in FIG. 44.

The advantage of the embodiment of FIG. 44 that it eliminates a long waveguide and the losses that occur when using a long waveguide. In this embodiment the suction housing would fit over the PZT stack and the ultrasonic horn. Certain useful ultrasound elements are depicted in U.S. Pat. No. 5,725,494 to Brisken, U.S. Pat. No. 5,069,664 to Zalesky, U.S. Pat. Nos. 5,269,291 and 5,318,014 to Carter, the contents of which are expressly incorporated by reference in their entirety.

Figure 45:
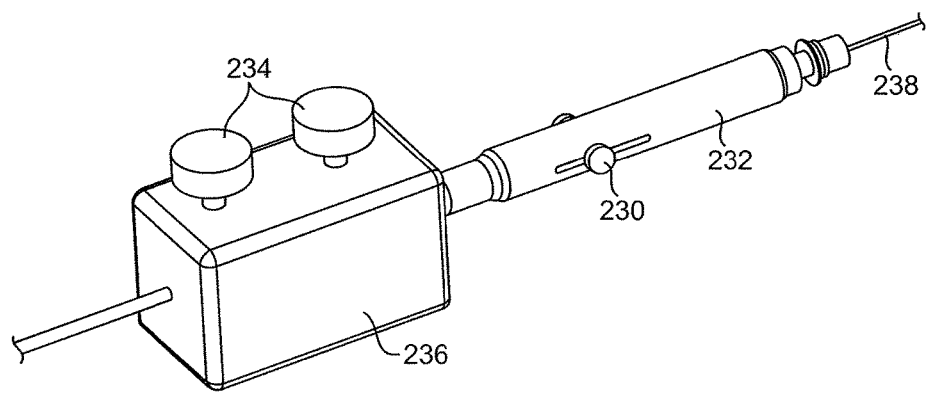
FIG. 45 illustrates a proximal housing for steering a distal end of the catheters of the present invention.

The proximal end of the ultrasonic catheter of the present invention may be configured according to the schematic depicted in FIG. 45. Knobs 230 on a proximal housing 232 are coupled to control wires that are connected to the distal end of the device. These knobs operate to tension the control wires thereby manipulating the angle of the distal end. Controls 234 for the steerable guide, such as gearing, pins, and shafts, are housed in the control box 236 on which the knobs are located. The main body of the treatment device further comprises an outer shaft and an inner shaft connected to slide knob. In turn the inner shaft is operatively connected at the distal end of the device to the housing such that when the slide knob is retracted the housing is translated from a retracted position to an extended position, or vice versa. Further depicted in FIG. 45 is a drive shaft or drive coil 230 that is operatively connected to an energy source or prime mover, for imparting motion to the drive coil. Drive coil terminates in the distal end of the device at the working element that contacts the tissue to be treated. Alternatively, in designs utilizing ultrasound, the ultrasonic waveguide or transmission element may be positioned within the outer shaft and/or inner shaft.

Mechanical Treatment Catheter and Methods

In addition to ultrasound treatment catheters described above, the present invention further provides treatment catheters and methods that use mechanically activatable tips to mechanically disrupt or obliterate the calcium on the leaflets. In general, the catheters will comprise a catheter body that comprises one or more lumens. A drive shaft (or similar element) may extend from a proximal end of one of the lumens to the distal end of the lumen. A distal working element may be coupled to (or formed integrally from) the drive shaft and will be configured to extend at least partially beyond a distal end of the catheter body. The proximal end of the drive shaft may be coupled to a source of mechanical motion (rotation, oscillation, and/or axial movement) to drive the drive shaft and distal working element.

The catheters of the present invention may use a variety of configurations to decalcify the leaflet. Some examples of the working elements and distal ends of the catheter body that may be used are described below.

Figure 46:
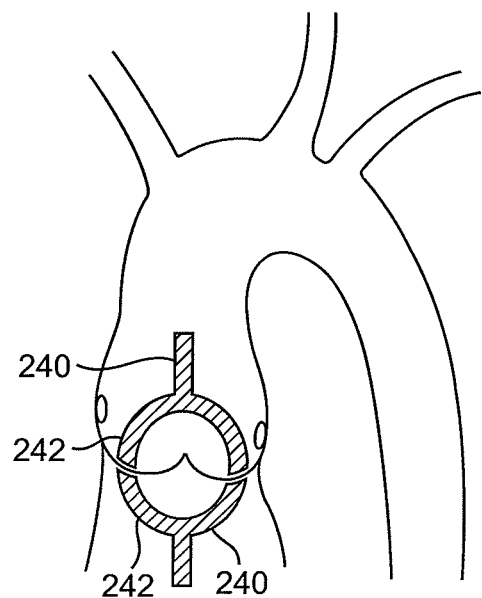
FIG. 46 illustrates use of a pair of suction catheters for treating a valve in accordance with the principles of the present invention.

In one embodiment (FIG. 46), the distal end of the catheter 240 comprises a suction housing 242 that may be used to contact and/or isolate the leaflet that is being decalcified. While the suction housing is illustrated as a funnel shaped element, in alternative embodiments, the suction housing may be of a similar shape as the leaflets that are to be treated (as described above). The suction housing 242 may be fixedly coupled to the distal end of the catheter body 240 or it may be movably coupled to the distal end portion. In such movable embodiments, the suction housing may be moved from a retracted position (not shown), in which the suction housing is at least partially disposed within the lumen of the catheter body, to an expanded configuration (shown below). Alternatively, a mechanical clip, clamp or other fixation element may be used to localize the treatment device at the annulus or leaflet to be treated such as that depicted below, including an element placed from the retrograde direction and the antegrade direction to secure the leaflets.

Figure 47:
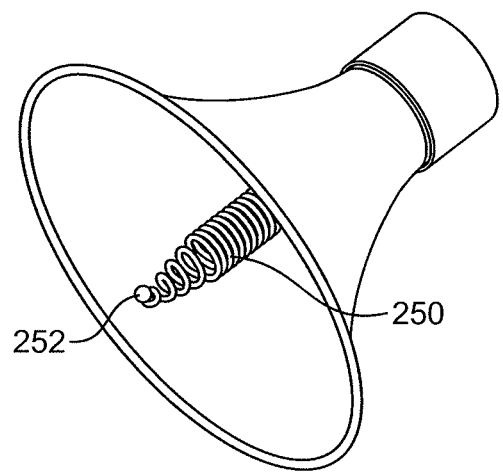
FIG. 47 illustrates a catheter having an eccentrically loaded coil in the working end thereof.

In the configuration of FIG. 47, the distal working element may comprise a rotatable, eccentrically loaded coil 250. The distal portion of the coil may taper in the distal direction and may comprise a ball 252 (or other shaped element) at or near its distal end. Optionally, one or more weighted elements (not shown) may be coupled along various portions of the coil to change the dynamics of the vibration of the coil. As can be appreciated, if the weight is positioned off of a longitudinal axis of the coil, the rotation profile of the coil will change. Consequently, strategic placement of the one or more weights could change the vibration of the coil from a simple rotation, to a coil that also has an axial vibration component.

Figure 48:
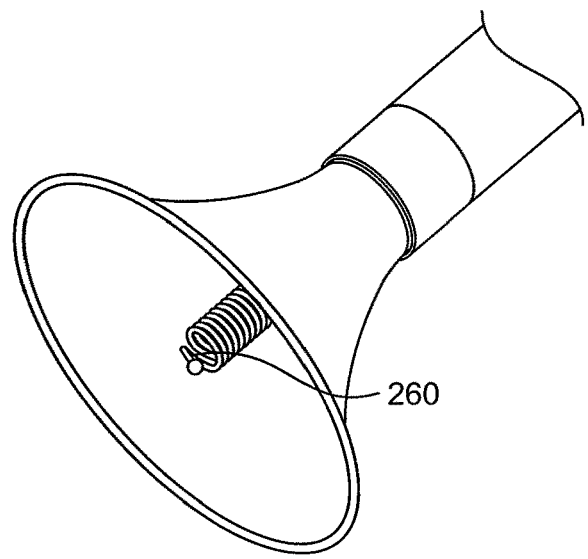
FIGS. 48 and 49 show variations on the coil of FIG. 47.

In another embodiment (FIG. 48), the working element may comprise an eccentrically loaded non-tapering coil 260. The coil may or may not comprise a ball or weight at its distal tip.

Figure 49:
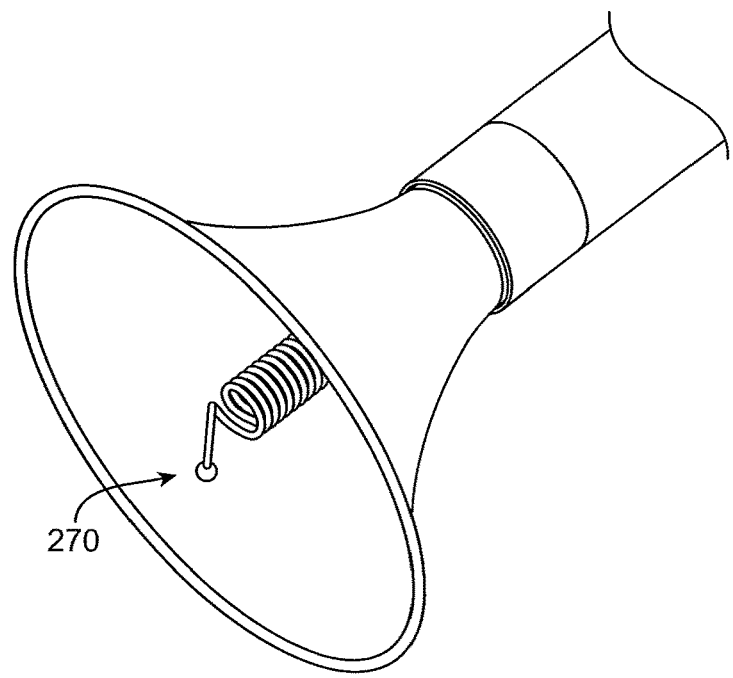

In yet another embodiment (FIG. 49), the distal coil may comprise an elongated distal wire tip 270 in which at least a portion extends radially beyond an outer diameter of the distal coil working element. As illustrated, the distal wire tip may comprise one (or more) balls or weights. The distal wire tip may be curved, straight or a combination thereof. As an alternative to (or in addition to) the aforementioned distal coils, the distal working element may comprise a "drill bit" type impeller or a Dremel type oscillating or rotating member at the distal tip that is configured to contact the calcification and mechanically remove the calcification from the leaflet. As can be appreciated, such embodiments will be rotated and oscillated in a non-ultrasonic range of operation, and typically about 10 Hz to 20,000 Hz, preferably 100 Hz to 1000 Hz. In such configurations, rotation of the shaped impellers will typically cause the calcification debris to be moved proximally toward the lumen in the catheter body. In some configurations, the impeller may comprise rounded edges so as to provide some protection to the leaflets. In each of the above mentioned embodiments, a sheath may cover the rotating elements to provide protection or to provide more directed force by transmitting the rotational and axial movements through the sheath.

Figure 50:
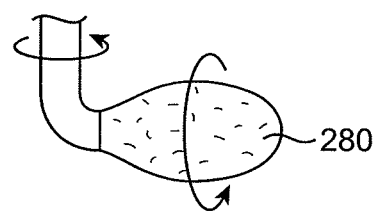
FIGS. 50-52 illustrate catheters having mechanical elements in their distal ends.
Figure 51:
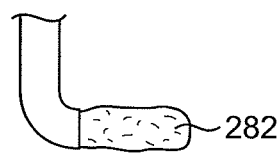
Figure 52:
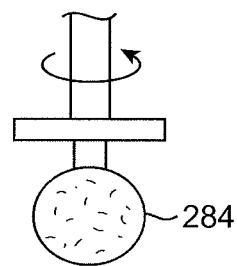

The working elements may also comprise mechanically rotating devices. In the embodiment of FIG. 50, an oval shaped burr 280 is shown that the orientation of which ranges from vertically aligned with the central axis of the device (rotating axis) to 90 degrees or more from the central axis of the device. This off axis orientation allows a range of debridement locations and may be more applicable for certain situations, such as stenoses that are located eccentrically within the valve annulus, or to treat leaflet surfaces that are angled with respect to the central axis of the device. Angulation of the treatment tip relative to the central axis of the treatment device facilitates fragmentation of the calcification by providing increased velocity at the tip region. A similar arrangement is shown in FIG. 51, but with a different shaped, more elongate burr 282. In addition, FIG. 52 shows a burr element 284 in the form of a disk having holes in the face of the disk to allow evacuation of debris through the burr element. It is within the scope of the present invention that any mechanical working elements may have a roughened surface, a carbide tip material, or diamond coating to enhance fragmentation of the targeted material. Representative burr elements are manufactured by several companies such as Ditec Manufacturing (Carpenteria, Calif.), Diamond Tool (Providence, R.I.), and Carbide Grinding Co. (Waukesha, Wis.).

Figure 53:
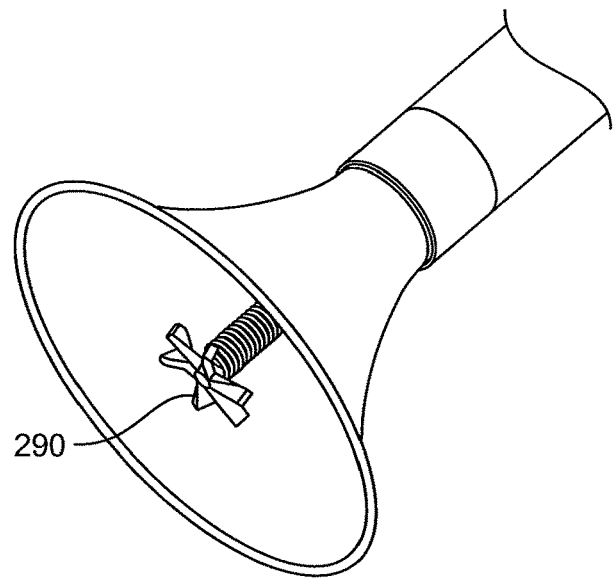
FIGS. 53 and 54 show catheters having distal impellers and grinders.

In alternative methods, it may be possible to position an impeller element 290 (FIG. 53) proximal to the aortic valve and not actually contact the leaflets. The rotation of the impeller may cause a vortex to remove calcific material off of the leaflet and into the suction housing and catheter body. The impeller may take a variety of forms such as the one described in U.S. Pat. No. 4,747,821 to Kensey, the contents of which are expressly incorporated herein by reference.

In another configuration, a rotating grinder head 292 (FIG. 54) may be coupled to the distal coil 294. The rotating grinder distal tip can take a variety of shapes. In the configuration illustrated below, the grinder distal tip is convex shaped and comprises a plurality of holes that are in a radial circular pattern around a central opening that is in communication with an axial lumen of the drive shaft. In such a configuration, the grinder distal tip is symmetrically positioned about the longitudinal axis of the distal coil and the rest of the drive shaft. The radial openings allow for irrigation and aspiration of particles. In some configurations, the grinder distal tip may comprise abrasive material, such as diamond dust, to assist in removal of the calcific material from the aortic valve.

Figure 55:
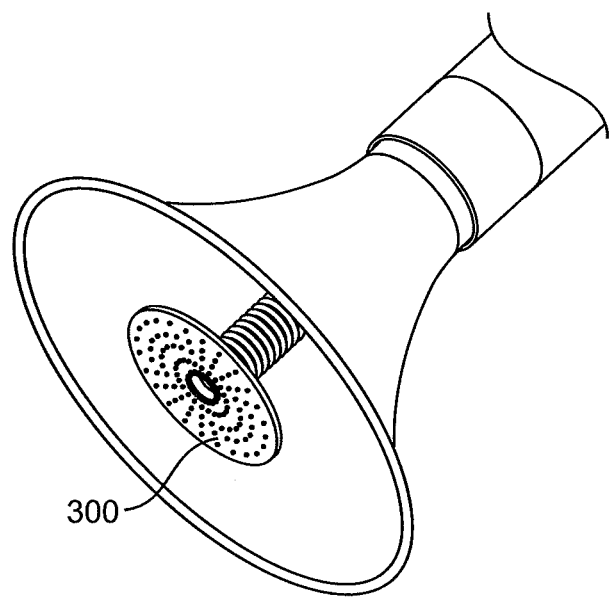
FIGS. 55-57 illustrate catheters having disk-like grinders with abrasive surfaces.
Figure 56:
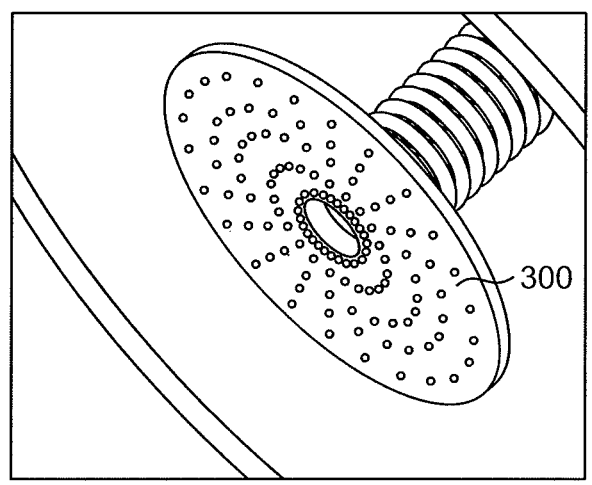

In another grinder distal tip configuration shown in FIGS. 55 and 56, the grinder distal tip may comprise a flat pate 300. The flat grinder distal tip may comprise an abrasive material, holes, and/or machined protrusions or nubs. Such elements may be used to enhance the calcification removal from the leaflet.

Figure 57:
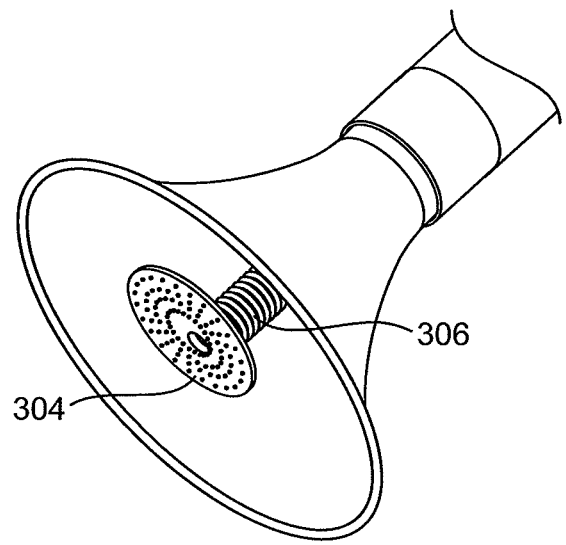

In an alternative configuration as shown in FIG. 57, a grinder distal tip 304 may be mounted eccentrically about the distal coil 306 so that upon rotation, the grinder tips may cover a greater surface area of the leaflet without having to enlarge the size of the grinder distal tip. The figure below illustrates the flat grinder distal tip, but it should be appreciated that any of the distal tips described herein may be mounted eccentrically with the distal coil.

In another embodiment, the distal working element may comprise a castellated mechanical tip, such as that shown above for the ultrasonic working element. Optionally, the castellated tip may have an impeller that is set back from the distal tip.

Figure 58:
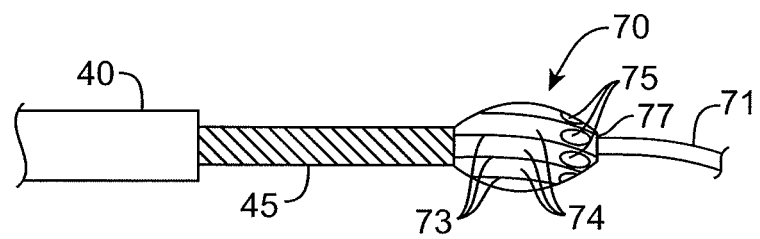
FIGS. 58 and 59 illustrate rotating burrs which may be placed in the distal end of the catheters of the present invention.
Figure 59:
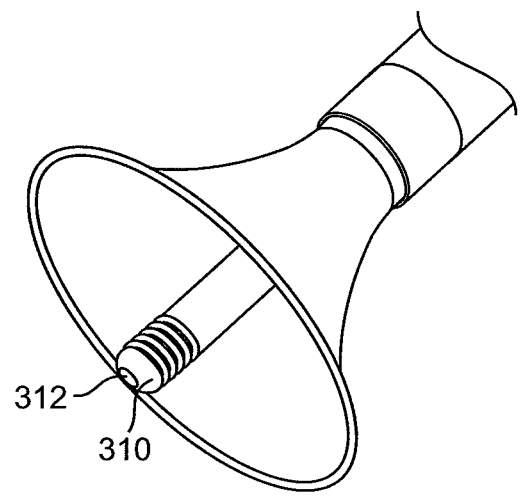

In yet another embodiment, the present invention may use the Rotablator device that is described in U.S. Pat. No. 5,314,407 or 6,818,001, the complete disclosure of which are expressly incorporated herein by reference, to decalcify a leaflet. The Rotablator (as shown below) may be used as originally described, or the distal tip may be modified by flattening the tip, applying diamond dust on the tip, making the distal tip more bulbous, or the like. See FIG. 58 which is taken from the '407 patent.

The air turbine used for the Rotablator may be used to power some or all of the aforementioned mechanically-based treatment catheters. The air turbine provides an appropriate amount of torque and speed for disruption of calcium on the leaflets. The torque and speed, combined with a low moment of inertia of the drive shaft and distal tips of the present invention, reduce the risk of catastrophic drive shaft failure. For example, when the distal tip becomes "loaded" due to contact with the calcific deposits, the speed of rotation will reduce to zero without snapping or wrapping up the drive shaft. As an alternative to the air turbine, it may also be possible to use a motor with an electronic feedback system that can sense torque and speeds such that the motor may be slowed down at appropriate times.

Figure 54:
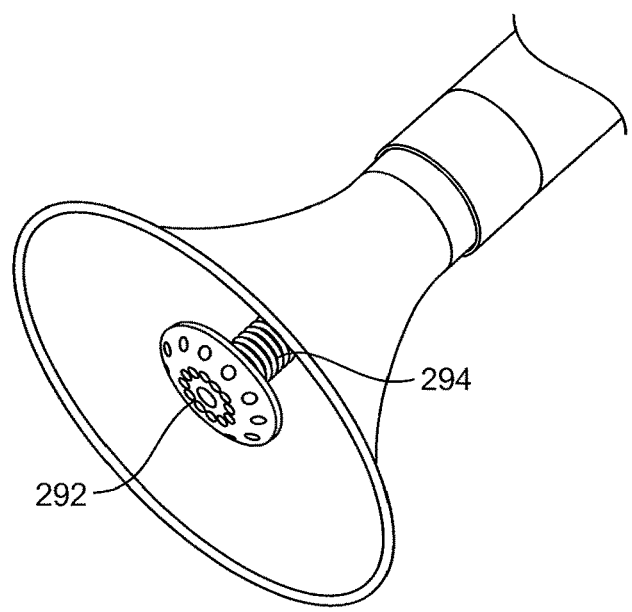

Some embodiments of the treatment catheter may comprise an optional sheath that surrounds the distal working element. As illustrated in FIG. 54, the sheath may comprise a spherical shaped distal tip 310 that surrounds the distal working element. An elongated proximal portion is attached to the spherical distal tip and is sized and shaped to cover some or all of the drive shaft that is within the lumen of the catheter body. The spherical shaped distal tip may comprise an opening 312 that will allow for the delivery of a media (e.g., contrast media, coolant, etc.) and/or for passageway of a guidewire. The mechanical element or ultrasonic transmission element may extend beyond the tip of the sheath. A similar depiction is shown in U.S. Pat. No. 6,843,797 to Nash, the contents of which are expressly incorporated herein by reference.

In some embodiments, the sheath may comprise bellows or a flexible portion that allows for the end of the sheath to bend, extend, and/or retract. The sheath will typically not rotate, and the sheath will typically be sized to allow the distal working element and the drive shaft to rotate within the sheath. Rotation of the distal working element within the sheath will articulate the sheath (which will depend on the shape and type of actuation of the drive shaft) and may create a "scrubbing effect" on the calcific deposits. Advantageously, the sheath will transmit the mechanical motion of the drive shaft, while providing a layer of protection to the leaflets by controlling the oscillation of the working element. The sheath may be made of a variety of materials as known in the art and reinforced in such a way as to withstand the friction from the rotation of the distal working element within the spherical distal tip Consequently, one useful material for the sheath is steel, or a braided or other catheter reinforcement technique.

In any of the mechanical embodiments, it may be desirable to circulate or inject a cooling fluid may be to decrease the heat energy seen by the tissue, and assist in the removal of debris during debridement. Such a fluid may also assist with tissue fragmentation by providing a cavitation effect in either the ultrasonic embodiments or the mechanical embodiments.

Virtual Decalcification Use of Microspheres and/or Microbubbles

As noted above, most embodiments of the ultrasound treatment catheters and the mechanical treatment catheters comprise a lumen that runs through the catheter body to the distal end. It may be useful to deliver a media, such as a cooling fluid, an ultrasound contrast fluid, or the like, through the lumen to the target leaflet to amplify the effect of the energy delivery to the embedded calcific nodules on the leaflet. In one preferred configuration, the media may comprise microspheres or microbubbles. One useful contrast media that may be used with the methods and treatment catheters of the present invention is the Optison™ contrast agent (GE Healthcare). Various depictions of techniques utilizing cavitation and/or microbubbles to enhance a therapeutic effect may be found in U.S. patent RE036939 to Tachibana, and U.S. Pat. No. 6,321,109 to Ben-Haim, the contents of which are expressly incorporated by reference herein in their entirety.

Delivery of the ultrasonic wave through the contrast media that contains the microbubbles can increase the amount of cavitation or fragmentation energy delivered to the leaflet. Applying suction during the procedure can also enhance the fragmentation energy as described by Cimino and Bond, "Physics of Ultrasonic Surgery using Tissue Fragmentation: Part I and Part II", Ultrasound in Medicine and Biology, Vol. 22, No. 1, pp. 89-100, and pp. 101-117, 1996. It has been described that the interaction of gas bodies (e.g., microbubbles) with ultrasound pulses enhances non-thermal perturbation (e.g., cavitation-related mechanical phenomena). Thus, using a controlled amount of contrast agent with microbubbles may enhance the removal of the calcification from the leaflets. A more complete description of the use of microbubbles with ultrasound energy is described in Guzman et al., "Bioeffects Caused by Changes in Acuostic Cavitation Bubble Density and Cell Concentration: A Unified Explanation Based on Cell-to-Bubble Ratio and Blast Radius," Ultrasound in Med. & Biol., Vol. 29, No. 8, pp. 1211-1222, 2003 and Miller et al., "Lysis and Sonoporation of Epidel moid and Phagocytic Monolayer Cells by Diagnostic Ultrasound Activation of Contrast Agent Gas Bodies," Ultrasound in Med. & Biol., Vol. 27, No. 8, pp 1107-1113, 2001, the complete disclosures of which are incorporated herein by reference.

It should be appreciated however, that the use of microbubbles are not limited to the ultrasound or mechanical treatment catheters. For example, as shown below, the contrast media may be used with an RF catheter or a piezoelectric-based catheter. In the RF catheter embodiment, the catheter body may comprise two RF electrodes positioned at or near the distal end of the catheter. The media with the microbubbles may be delivered to the target leaflet through the lumen of the catheter, and an RF energy may be delivered between two leads to deliver energy to the microbubbles. In some embodiments, it may be desirable to deliver RF energy to the calcification on the leaflets without the use of the microbubbles. In other embodiments, it may be desirable to use other types of energy sources to deliver energy to the leaflets.

Figure 60:
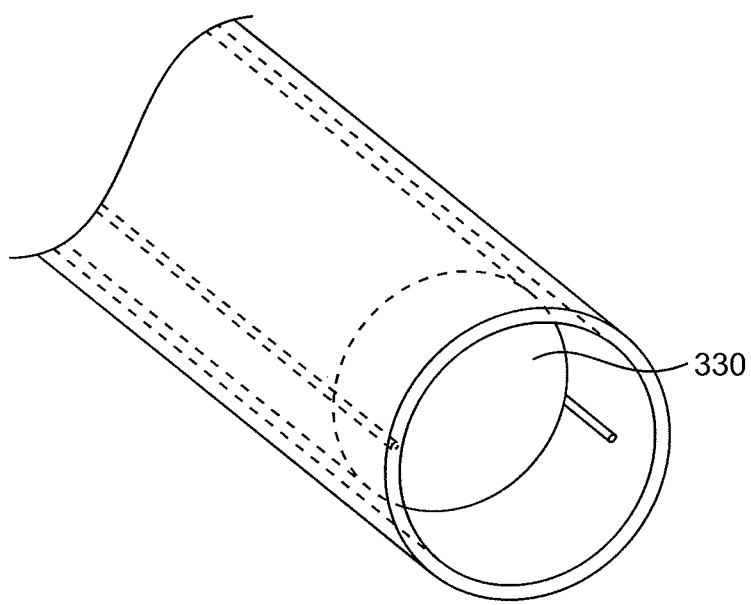
FIG. 60 illustrates a catheter having a piezoelectric film element in its distal end.

As an alternative to RF electrodes, it may be possible to position a piezo film 330 at the distal tip of the catheter (FIG. 60). Wire leads will extend through, within (or outside) the lumen of the catheter body and will be coupled to a generator. If the wire leads are disposed within the lumen of the catheter body, the catheter may comprise an inner tube to insulate the wires. The media may be delivered through the inner lumen of the catheter body and exposed to the piezo film at the distal end of the catheter body, and the energy may be delivered from the piezo film and into the media with the microbubbles.

Protection

Figure 61:
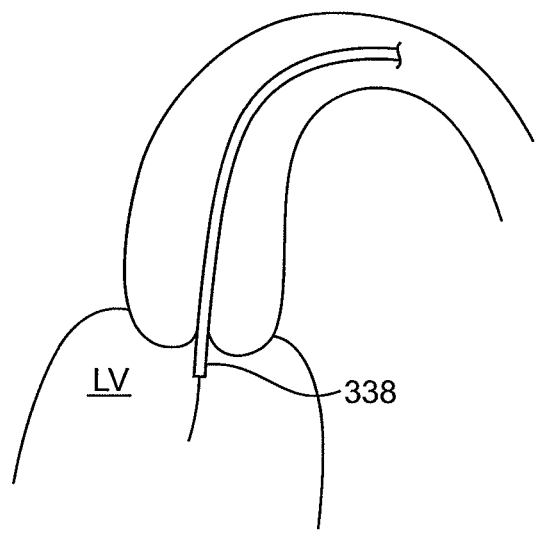
FIGS. 61 and 62 show guiding catheters having filter elements at their distal ends which are used for introducing the catheters of the present invention.
Figure 62:
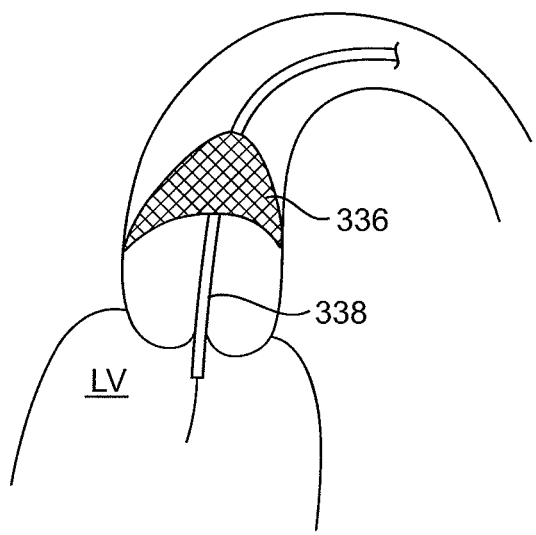

In a further aspect of the present invention, protection devices and methods may be used to trap and evacuate debris from the treatment site. In one embodiment shown in FIGS. 61 and 62, a filter device 336 is located on the shaft of a guide catheter 338. This structure may also provide anchoring of the guide catheter in the aortic root to provide a stable access system to the valve or placing additional treatment catheters.

Figure 63:
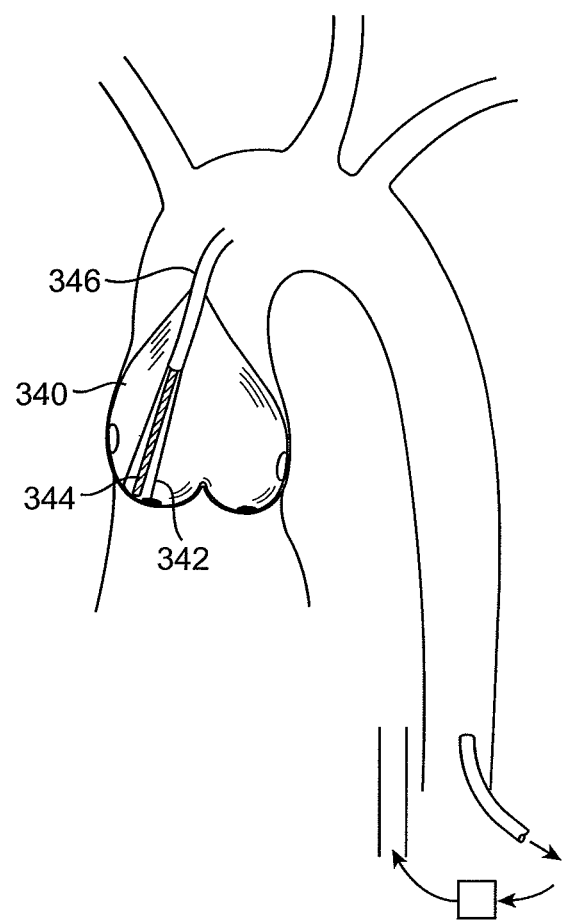
FIG. 63 illustrates a filter device deployed to protect an entire region of treatment.

In another embodiment (FIG. 63), a filter device is deployed to protect the entire region of treatment and may include a systemic filtering device 340 such as those where blood and aspirate are removed from the arterial side of the vasculature, filtered and then infused back into the venous circulation, further details in U.S. Pat. No. 6,423,032 to Parodi, the disclosure of which is expressly incorporated herein by reference. A suction port 342 surrounds the ultrasound probe 344 at the distal end of catheter 346.

Figure 64:
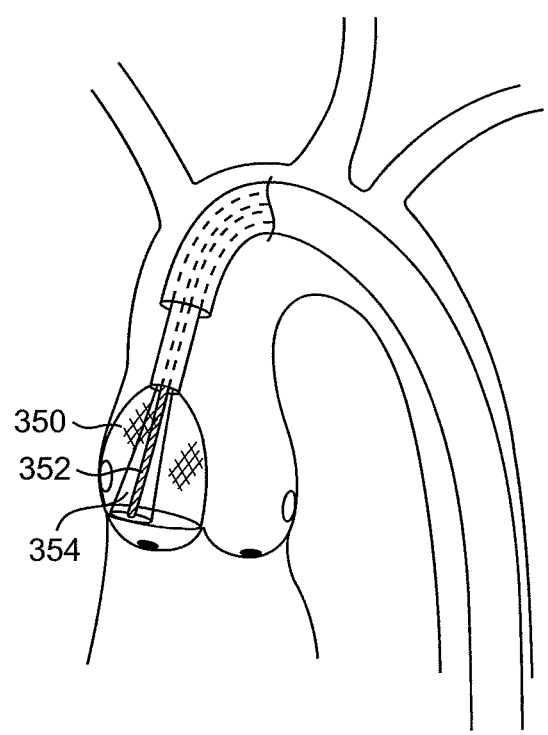
FIG. 64 illustrates a filter device covering a single leaflet.

It may be advantageous to have filtering applied more locally closer to the treatment site (e.g. one leaflet at a time), to protect local structures such as the ostium of the coronaries located just above the aortic valve. Such a filtering device may be used in conjunction with treatment devices, such as the ultrasonic suction catheter shown in FIG. 64, where filter device 350 covers a single leaflet which is also engaged by ultrasonic probe 352 at suction port 354. Further, the filter shape may be optimized to access the most relevant leaflet or treatment site, as shown in FIG. 6. Any of the above filtering or protection systems may be used with any of the treatment catheters disclosed herein.

Numerous features of the present invention aid in directing, positioning and stabilizing the treatment catheter optimally at the site of the disease to be treated. In addition to catheter and guide features, baskets, anchor or filter configurations that seat within the valve, certain methods may be used to position the catheter. For example, the heart may be connected to a pacing lead and the heart then paced at an increased rate, for example 200 beats per minute, which then holds the aortic leaflets in a relatively fixed location arresting blood flow and allowing the treatment catheter of the present invention to be applied to at least one leaflet. Following placement of the catheter, such as a suction housing, pacing is stopped, and the remaining leaflets not engaged by the catheter, function normally. In the event that all leaflets are engaged at once, it may be necessary to provide flow through the treatment catheter, such as in a perfusion balloon or device known in the art, some features of which are shown in U.S. Pat. No. 4,909,252 to Goldberg the disclosure of which is expressly incorporate by reference herein.

Imaging

Features of the present invention include various devices and methods for monitoring and imaging prior to, during and post procedure. Various imaging modalities may be employed for this purpose, including intracardiac echocardiography (ICE), transesophageal echocardiography (TEE), fluoroscopy, intravascular ultrasound (IVUS), angioscopy, infrared, capacitive ultrasonic transducers (cMUTs) available from Sensant, Inc./Seimens (San Leandro, Calif.) or other means known in the art. For example the treatment catheter may have an imaging device integrated into the housing or treatment element catheter shaft, such as a phased array intravascular ultrasound element. In some embodiments it may be advantageous to construct the device of the present invention so that they working element is a separate, removable element that is coaxial with the sheath to enable the operator to remove the working element and place an imaging element in its place.

Imaging may become critical at various stages of the procedure, including diagnosing the type and location of the disease, placing the treatment catheter, assessing the treatment process, and verifying the function of the valve once it is treated. Imaging devices may be placed locally at the treatment site, such as on the catheter tip, or catheter body, alongside the treatment catheter, or in more remote locations such as known in the art (e.g. superior vena cava, esophagus, or right atrium). If the imaging element is placed on the treatment catheter, it may be adapted to be "forward looking" e.g. image in a plane or multiple planes in front of the treatment device.

It is also within the scope of the present invention to employ interrogation techniques or other imaging modalities, such as infrared imaging to see through blood for direct visualization of the treatment site, or elastography, the ultrasonic measurement of tissue motion, to sense what type of tissue is targeted, e.g. leaflet tissue or calcium, or to sense the region of the valve that is most calcified. Elastography in this context may be performed using an intravascular ultrasound (IVUS) catheter, either a mechanical transducer or phased array system, such as those described in "Characterization of plaque components and vulnerability with intravascular ultrasound elastography" Phys. Med. Biol. 45 (2000) 1465-1475, the contents of which is expressly incorporated by reference herein. In practice, the transducer may be advanced to a treatment site on the valve, and using either externally applied force, or "periodic excitation" of the tissue region either by externally applied force or the naturally occurring movement in the tissue itself (such as the opening and closing of the valve leaflets), an initial baseline reading can be taken. This baseline could be set by engaging the region or leaflet to be treated with a suction catheter of the present invention (including circulating fluid within the treatment site), inserting an ultrasound transducer through the treatment catheter up to the treatment site, and interrogating the targeted region with the ultrasound transducer to establish the elasticity of the region (stress/strain profile). For a particular region of the leaflet, infusion can then be stopped, putting the leaflet under additional stress (by suction alone) and the displacement in the stress/strain profile can be noted and evaluated to direct the treatment device to those locations showing less elasticity ("stiffer" regions indicating the presence of calcific deposits. See also those techniques set forth in "Elastography—the movement begins" Phys. Med. Biol. 45 (2000) 1409-1421 and "Selected Methods for Imaging Elastic Properties of Biological Tissues" Annu Rev. Biomed. Eng. (2003) 5:57-78, the contents of which are expressly incorporated by reference herein.

In some instances, for example with ultrasound or laser, the same transducer or fiber optic that is used to interrogate or image the region may also be used to break up or treat the underlying calcific deposits. Certain parameters may be adjusted to transition the therapy device from diagnostic to therapeutic, including frequency, power, total energy delivered, etc.

In addition, other characterization techniques may be employed to both target the calcific region to be treated or assess the result of a treatment, including MRI, Doppler, and techniques that utilize resistivity data, impedance/inductance feedback and the like. Using imaging and other monitoring techniques such as those described, can result in a more targeted procedure that focuses on removing calcific deposits and limits potential tissue damage to the leaflet and annulus that can lead to an unwanted proliferative response.

Energy Sources/Methods of Treatment

A variety of energy modalities may be used in the treatment catheters envisioned by the present invention. Those modalities more specifically useful for breaking down or obliterating calcific deposits may be ultrasonic energy, laser energy and the like. Specifically, some Er:YAG lasers may specifically target calcium when operated in appropriate ranges. Some detail of targeted bone ablation supports this as found in "Scanning electron microscopy and Fourier transformed infrared spectroscopy analysis of bone removal using Er:YAG and CO2 lasers" J Periodontol. 2002 June; 73(6):643-52, the contents of which are expressly incorporated by reference herein. Alternatively, energy may be delivered to selectively remove tissue from around or over a calcium deposit by employing a resurfacing laser that selectively targets water-containing tissue resulting in controlled tissue vaporization, such as a high-energy pulsed or scanned carbon dioxide laser, a short-pulsed Er:YAG, and modulated (short-and-long-pulsed) Er:YAG system. This application of energy may be useful for accessing plaque or calcium that is distributed between the leaflets (spongiosa). In practice, it would be desirable to remove the layer of tissue covering the deposit so that the majority of the leaflet remained intact and shielded from unnecessary thermal damage. Further, such specific tissue destruction may also be applied to the removal of scar tissue or regions of hypertrophy within the valve annulus as part of the treatment of the present invention.

The ultrasonic treatment catheters of the present invention may be operated in ranges between 5 and 100 kHz, for example 10-50 kHz, with an oscillation rate in the range of 10-200 microns, for example 75-150 microns (maximum travel between 20-400 microns). In addition, to minimize potential for thermal damage or other tissue damage, it may be advantageous to operate the treatment devices in a pulsed manner, such as a 5-50% duty cycle, for example a 5-20% duty cycle, and to minimize the tissue that is exposed to the energy application by carefully targeting the delivery of energy to the most diseased regions.

Figure 67:
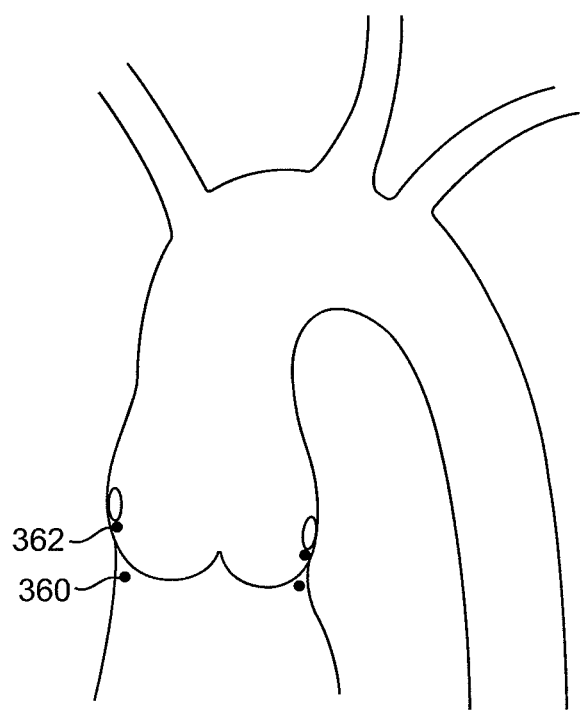
Figure 68:
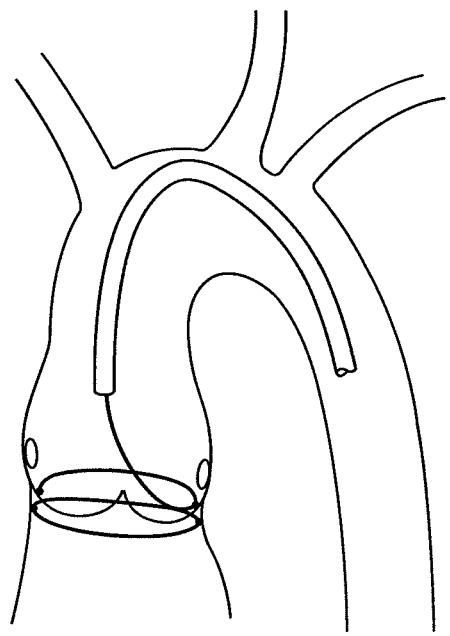

In addition, it may be advantageous to focus the treatment on certain locations of the diseased valve where removing or reducing calcium deposits result in the greatest amount of restored leaflet mobility and resulting valve function. For example, deposits within the annulus of the valve, at the nadir of the leaflet, in the mid-section of the leaflet, or at the commissures may be initially targeted. A schematic depiction of these various positions with the valve are depicted in FIGS. 66, 67, and 68, where FIGS. 67 and 68 are cross-sections along lines A-A and B-B of FIG. 66, respectively.

Depending on the type and frequency of energy used, the treatment catheters of the present invention may also be utilized to not only remove calcium, but also to remove or obliterate the leaflet itself, such as in preparation for implantation of a minimally invasive prosthetic valve, such as those disclosed in U.S. Pat. Nos. 5,840,081 and 6,582,462 to Anderson, US Patent Application 2004/0092858 to Wilson, PCT Publication WO 2004/093728 to Khairkhahan, WO 2005/009285 to Hermann and the like, the disclosures of which are expressly incorporated herein by reference. Pre-treatment with devices of the present invention may facilitate placement of such prosthetic valves since removing calcium from the site of implantation may reduce perivalvular leak, dislodgement, and may result in a larger prosthesis being implanted due to an increased effective valve orifice.

Implantable Devices

A. As an alternative or adjunct to the devices described above which are removed once the repair is achieved, devices may be provided which are temporarily or permanently implanted across or within the aortic valve. The devices which appear below are all intended to remain for at least a period of time within the body after the repair of the stenosis has been completed in order to prevent or delay the valves from degenerating, by either recalcifying, fusion of leaflets, and restenosing. An implant of the present invention is depicted in FIG. 67 in either a sub annular 360 or supra annular position 362.

Figure 69:
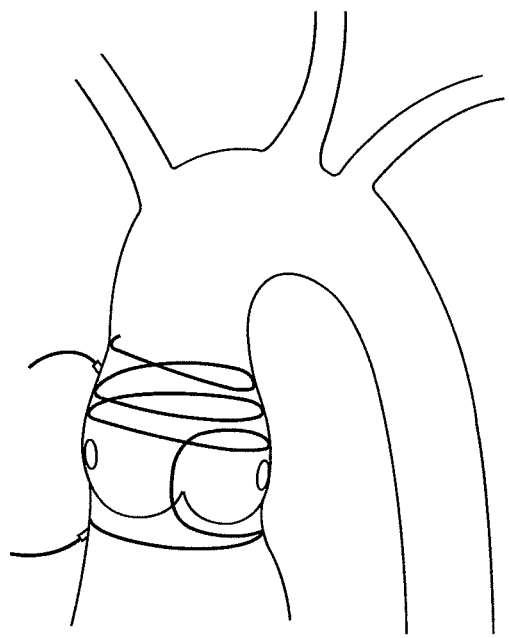
FIG. 69 shows a device having an open lattice structure.

In some embodiments, it may be desirable to place an implant such as the coil depicted below, to extend both sub annular and supra annular to provide additional support to the valve and provide a greater treatment area across the valve. The coil design of this embodiment has a single strut that joins the two ring portions but is low profile enough that is does not occlude the coronaries just above the valve annulus. See, FIG. 68. Because of its open structure, the supra annular portion of the implant can extend above the coronaries into the aortic root for additional anchoring. See, FIG. 69.

Figure 70:
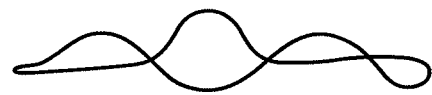
FIGS. 70-72 show implants formed from lattice wire structures.
Figure 71:
Figure 72:
Figure 73:
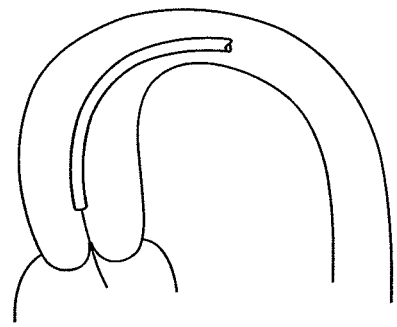
FIGS. 73-76 illustrate implants having multiple loops.
Figure 74:
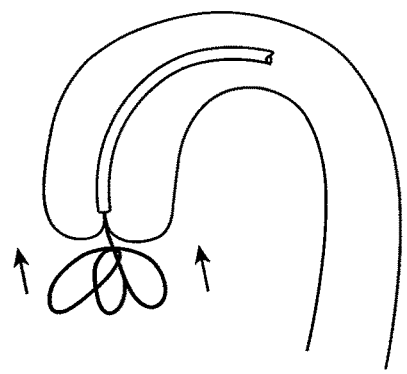
Figure 75:
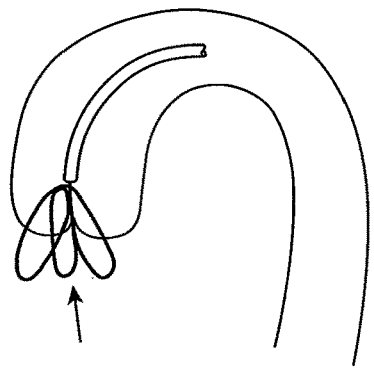
Figure 76:
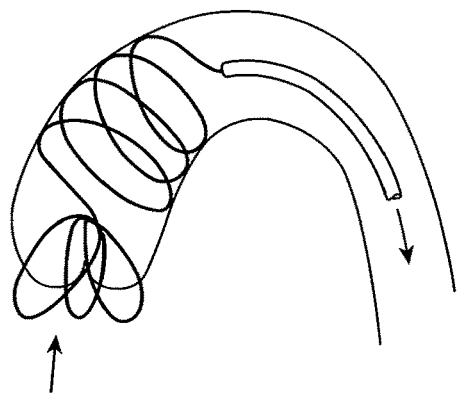

In a further embodiment, the implant may be formed of a wire, series of wire, or cellular structure similar to that used in peripheral or coronary stents. To better seat in the valve annulus, or below the valve, it may be advantageous to form the implant ring to follow the cusps of the valve, in a sinusoidal form. In addition, the implant ring may have struts that extend to seat against the annulus of the valve to provide structure or further disseminate a pharmacologic coating at specific valve sites. See, FIGS. 70, 71, and 72.

In yet another embodiment, the implant may be formed of multiple loops, such as three loops 120 degrees from each other. See, FIGS. 73-76.

In this embodiment, and others depicting wire forms, the wire may have a diameter between 0.020" and 0.250" depending on the force desired. In addition, the wire may be flat and the structure may include a mesh between the loops to provide a larger surface area for supporting the valve or delivery the pharmacologic agent. The loops of this device may be moved distally and proximally in a cyclic way to further open the valve leaflets and disrupt plaque as a stand alone therapy. The device may then be permanently implanted as detailed above. It may be desirable to recapture the device, either once the valve has been treated, or during positioning of the permanent implant to ensure proper placement. A recapture device may be the delivery catheter from which the implant is deployed, or may include an expandable funnel on the distal end of a retrieval catheter or may include any number of mechanical devices including a grasper or a hook that mates with a hook on the implant, or grasps the implant at some point such that it may be drawn into the delivery sheath and removed from the body.

The structure of any of the implants described herein may have surface enhancements or coatings to make them radiopaque or echogenic for purposes of procedure assessment as is known in the art. As is further known in the art in the field of coronary artery stenting, the devices described may be permanent, removable, or bio-erodable. They can incorporate anti-restenosis agents or materials such as those set forth above, in the form of coatings, holes, depots, pores or surface irregularities designed into or applied onto the devices. In addition, the implants can be formed of certain calcification resistant materials such as those set forth in U.S. Pat. No. 6,254,635, the contents of which are expressly incorporated by reference herein. Further, implants of the present invention may be configured to emit a slight electrical charge. Since calcium is positively charged, it may be advantageous to repel calcium by positively charging the surface of the aortic implant. In addition, electrical energy may be supplied by the implant to minimize calcification by an implantable pacemaker type device as described in U.S. Pat. No. 6,505,080, which is expressly incorporated by reference herein.

Further, it is within the scope of the present invention to combine certain mechanical procedures and implants with various appropriate pharmacologic agents such as those listed previously. Anti-restenosis agents which may be useful in this application may be chosen from any of the families of agents or energy modalities known in the art. For example, pharmaceutical agents or their analogues such as rapamycin, paclitaxel, sirolimus or nitric-oxide enhancing agents may be coated onto these devices using drug eluting coatings, incorporated into intentionally created surface irregularities or specific surface features such as holes or divots. The devices may be designed for drug infusion through the incorporation of coatings or other surfaces to adhere the agents to the implants utilized to perform the procedures of the present invention, or may be prescribed for oral administration following procedures of the present invention. For example, following a treatment of the present invention, a patient may be prescribed a dose of statins, ACE inhibitors or other drugs to prolong the valve function provided by the intervention.

FIGS. 77-89 represent various embodiments of systems intended for acute or sub-chronic procedures. These devices may be placed across the aortic valve and expanded to reopen the aortic valve, and then left in place for a period of time in order to expose the treated valve to anti-restenosis agents or energy modalities designed to facilitate the repair and/or to prevent restenosis. The device shown in FIGS. 77 and 78 features mechanical vanes 400 which extend outward to engage and separate the fused leaflets at the commissures. The vanes may be made of any suitable metal, plastic or combination. They may be self expanding (made from nitinol or elgiloy, for instance) or they might be mechanically actuated using a pneumatic, hydraulic, threaded or other mechanical actuation system. The vanes might be deformable members as shown above, or each vane might be made up of several more rigid parts connected at hinged portions to allow expansion and contraction of the unit. The vanes may be designed with a cross section which is rectangular in shape, with the narrower edge designed to facilitate separation of fused leaflets and to fit within the commissures without impacting the ability if he valves to close. The wider face of these rectangular vanes would contact the newly separated edges of the leaflets. As an alternative to the rectangular cross section, the vanes might be designed to have more of a wing-shaped or other cross sectional shape to minimize turbulence within the bloodstream and to minimize trauma to the valve leaflets.

Figure 79:
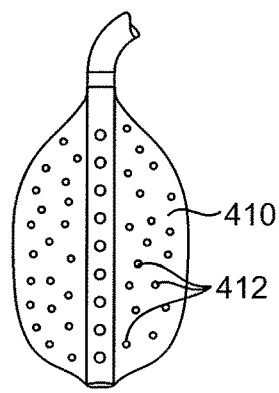
Figure 80:
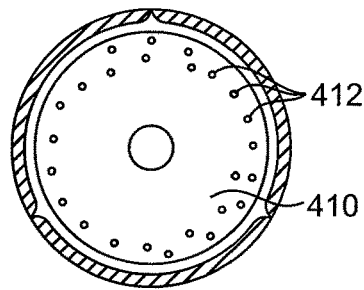

The device of FIGS. 79 and 80 shows a balloon system to be used in accordance with the inventive methods. The balloon 410 may feature a plurality of holes 412 to be used for the infusion of anti-restenosis agents as described in more detail below. These holes maybe small enough to allow only a slight weeping of the agents to be infused, or they might be of a size which would allow more rapid infusion or a greater volume of infusate to be delivered. The holes might be placed in even distribution around the circumference of the balloon, or they might be placed to align more directly with the location of the commissures.

Figure 77:
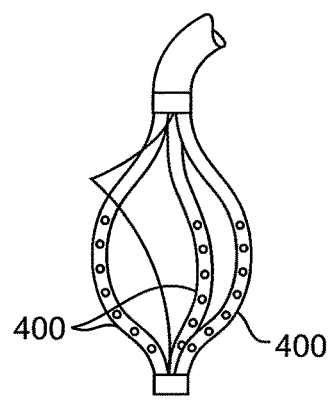
FIGS. 77-80 show embodiments of the present invention for delivering drugs to the target treatment sites.
Figure 78:
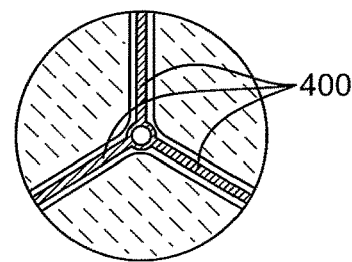
Figure 81:
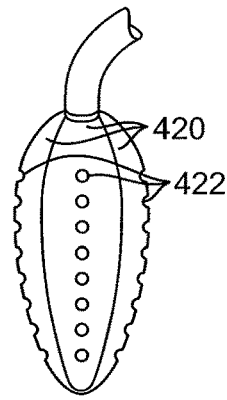
FIGS. 81 and 82 illustrate catheters having balloons with both drug release capability and blood perfusion capability.
Figure 82:
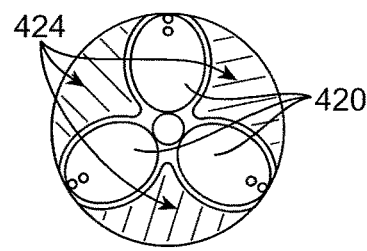

The device of FIGS. 81 and 82 comprise a balloon system which combines features of FIGS. 77 and 78 with those of 79 and 80. Several balloons are placed such that each balloon aligns with a commissure 424. Inflation of this device may allow continued perfusion of blood out of the heart and into the body which the device is in place. This in turn might low for more prolonged delivery of anti-restenosis agents. Holes might be placed on the balloons of FIG. 3 similar to the description for the holes on the device in FIGS. 79 and 80.

Anti-restenosis agents which may be useful in this application may be chosen from any of the families of agents or energy modalities known in the art. For example, pharmaceutical agents or their analogues such as rapamycin, paclitaxel, sirolimus or nitric-oxide enhancing agents may be coated onto any of the inventive devices using drug eluting coatings, incorporated into intentionally created surface irregularities or specific surface features such as holes or divots. As described, the devices may be designed for drug infusion through the incorporation of infusion channels and infusion holes in the work-performing elements of the devices such as the balloons or commissurotomy vanes shown in the drawings.

Energy delivery may be achieved by several different modalities and for different purposes. Radiofrequency energy can be applied by energizing the commissurotomy vanes or by using the pores on the balloons to achieve a wet electrode. Microwave, ultrasound, high frequency ultrasound energy or pulsed electric fields (for the purpose of inducing cellular electroporation) might be used by incorporating antennae or electrodes into the vanes, balloons or catheter shafts that support these work performing elements. Cryotherapy can be achieved by circulating cooling fluids such as phase-change gases or liquid nitrogen through the work performing elements. Multiple modalities might be incorporated into a single device for achieving the goal of durable aortic valve repair.

This energy may be used to facilitate the valve repair, for instance by making easier the parting of fused leaflets. Alternatively, the energy may be used to delay or prevent restenosis of the treated valve. One example of the use of energy delivery for the prevention of restenosis is the use of pulsed electric fields to induce cellular apoptosis. It is known in the art that the application of pulses of electricity on the order of nanosecond duration can alter the intracellular apparatus of a cell and induce apoptosis, or programmed cell death, which is known to be a key aspect of the mechanism of action of the clinically proven anti-restenosis drugs such as paclitaxel or sirolimus.

These agents or energy applications might be administered while the patient is in the catheterization lab, over the course of minutes to hours. Alternatively, the devices may be designed to allow the patient to return to the hospital floor with the device in place, so that the infusion of agents or the application of energy could proceed over the course of hours or days.

B. As an alternative or adjunct to the devices described above which are removed once the repair is achieved and administration of the anti-restenosis agents is completed, devices may be provided which are temporarily or permanently implanted across or within the aortic valve. The devices which appear below are all intended to remain for at least a period of time within the body after the repair of the stenosis has been completed in order to prevent or delay the valves from readhering to one another and restenosing.

Figure 83:
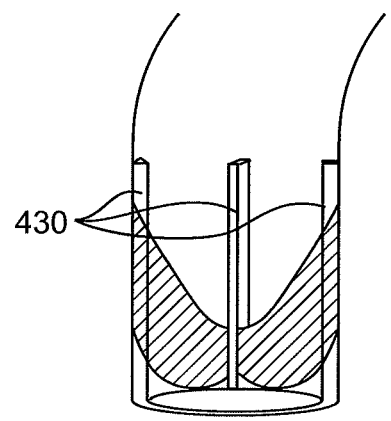
FIGS. 83 and 84 show implantable devices having deployable struts.
Figure 84:
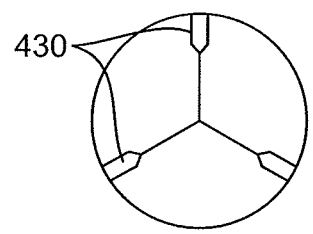
Figure 85:
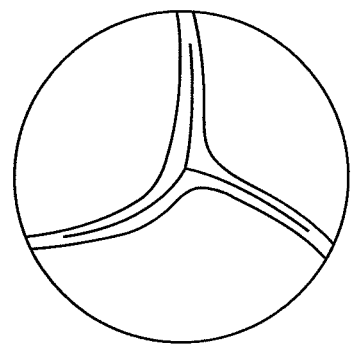
FIGS. 85 and 86 show implantable devices having anchoring elements which lie against the wall of the aorta.
Figure 86:
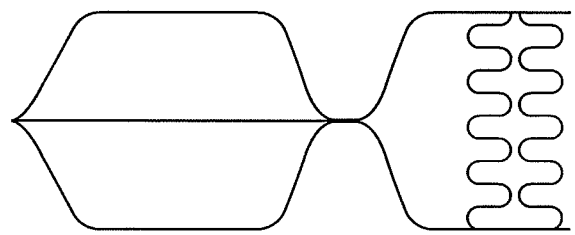
Figure 87:
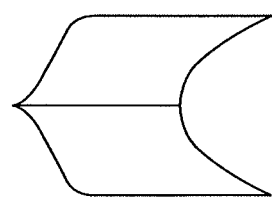
FIGS. 87-89 show embodiments where the device struts also provide for anchoring.
Figure 88:
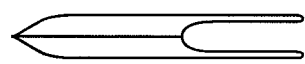
Figure 89:
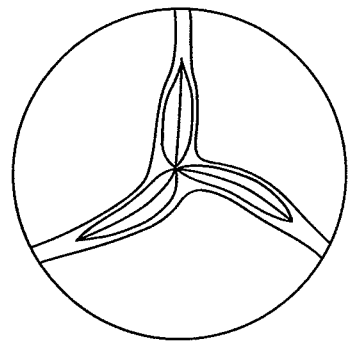

The devices described may be permanent, removable, or bio-erodable. They can incorporate anti-restenosis agents or materials into coatings, holes, depots, pores or surface irregularities designed into or applied onto the devices The struts 430 may be made of any suitable metal, plastic or combination as shown in FIGS. 83 and 84. They may be self expanding (made from nitinol or elgiloy, for instance) or they might be mechanically actuated during implantation using a pneumatic, hydraulic, threaded or other mechanical actuation system and then locked into their final position prior to deployment of the device from the delivery system. The struts might be deformable members as shown above, or each strut might be made up of several more rigid parts connected at hinged portions to allow expansion and contraction of the unit. The struts may be designed with a cross section which is rectangular in shape, with the narrower edge designed to facilitate separation of fused leaflets and to fit within the commissures without impacting the ability if he valves to close. The wider face of these rectangular struts would contact the newly separated edges of the leaflets. As an alternative to the rectangular cross section, the struts might be designed to have more of a wing-shaped or other cross sectional shape to minimize turbulence within the bloodstream and to minimize trauma to the valve leaflets.

FIGS. 85-89 show alternate designs for the implantable device. It should be noted that any design for the implant which achieves the goals of providing long-term anti-restenosis agents or energy modalities to the treated regions of the repaired leaflets should be considered as subjects of this invention. Anchoring elements which lie against the wall of the aorta and are generally contiguous with the struts (as shown in FIGS. 83 and 84), which join in the center of the aorta before reforming with the struts (as in FIGS. 85 and 86), or designs in which the struts themselves are the anchoring elements (as in FIGS. 87-89) are all embodiments of the subject invention.

The implantable and bio-erodable devices might all feature pharmaceutical agents or their analogues such as rapamycin, paclitaxel, sirolimus or nitric-oxide enhancing agents, which may be coated onto any of the inventive devices using drug eluting coatings, or incorporated into intentionally created surface irregularities or specific surface features such as holes or divots.

Additional anti-restenosis agents or energy modalities might be delivered separate from and/or in addition to those agents that are incorporated onto the implant, for instance as a feature of the delivery system.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the disclosure and appended claims.

What is claimed is:

1. An apparatus, comprising:
a catheter configured for intravascular placement within a body lumen of a human patient,
wherein the catheter comprises an expandable distal basket formed from a plurality of elongate members;
wherein the distal basket is transformable between—
a low-profile delivery configuration, and
an expanded deployed configuration wherein one or more of the elongate members of the distal basket contact a wall of the body lumen and are arranged such that blood is allowed to flow therethrough; and
a plurality of electrodes arranged along the elongate members of the basket and adapted to be positioned into contact with the wall of the body lumen when the basket is in the deployed configuration, wherein at least two of the electrodes are at different longitudinal positions along the basket, and wherein the electrodes are configured to deliver an electric field to target tissue adjacent the body lumen,
wherein the distal basket comprises a plurality of infusion ports or outlets distributed along each of the elongate members of the basket and configured to allow infusion of a pharmaceutical agent into the body lumen, and wherein the plurality of infusion ports or outlets are interspersed among and distinct from the plurality of electrodes arranged along the elongate members of the basket.

2. The apparatus of claim 1 wherein the elongate members of the distal basket are fabricated from shape-memory material.

3. The apparatus of claim 1 wherein the elongate members of the distal basket are composed, at least in part, of a metal material.

4. The apparatus of claim 1 wherein the elongate members of the distal basket are composed, at least in part, of plastic.

5. The apparatus of claim 1 wherein the basket is collapsible for delivery to the body lumen within a guide catheter, and further wherein the basket is configured to self-expand into contact with the wall of the body lumen upon removal from the guide catheter.

6. The apparatus of claim 1 wherein the basket is collapsible for delivery to the body lumen within a guide catheter, and further wherein the basket is configured to be mechanically actuated to transform the basket from the low-profile delivery configuration into the expanded deployed configuration.

7. The apparatus of claim 1 wherein the electrodes are arranged in a staggered configuration along the members of the basket, and wherein the electrodes are configured to be energized to produce a plurality of treatment areas along the wall of the body lumen.

8. The apparatus of claim 1 wherein the electric field delivered by the electrodes comprises a non-pulsed thermal RF electric field.

9. The apparatus of claim 1 wherein the electric field delivered by the electrodes comprises a pulsed electric field.

10. The apparatus of claim 1 wherein a plurality of electrodes are carried by each elongate member of the basket.

11. The apparatus of claim 1 wherein the infusion ports or outlets are configured to allow infusion of the pharmaceutical agent before, during, and/or after delivery of electrical energy to the target tissue.

* * * * *